United States Patent [19]

Alessi et al.

[11] Patent Number: 4,897,405
[45] Date of Patent: Jan. 30, 1990

[54] NOVEL NAPHTHALENYLALKYL-3H-1,2,3,5-OXA-THIADIAZOLE 2-OXIDES USEFUL AS ANTIHYPERGLYCEMIC AGENTS

[75] Inventors: Thomas R. Alessi, Middlesex County, N.J.; Terence M. Dolak, Ontario County, N.Y.; John W. Ellingboe, Mercer County; Louis J. Lombardo, Middlesex County, both of N.J.

[73] Assignee: American Home Products Corporation, New York, N.Y.

[21] Appl. No.: 341,340

[22] Filed: Apr. 21, 1989

[51] Int. Cl.$^4$ .................... C07D 291/04; A61K 31/41
[52] U.S. Cl. ..................................... 514/360; 548/122
[58] Field of Search ......................... 548/122; 514/360

[56] References Cited

U.S. PATENT DOCUMENTS 4,148,801  4/1979  Santilli .............................. 564/224

OTHER PUBLICATIONS

Dondoni, J. Org. Chem. 42 3372 (1977).
Eloy, Bull. Soc. Chim. Belg. 74, 129 (1965).
A. Dondoni et al., J. Org. Chem., 42 (21), 3372–3377 (1977).
A. Y. Chang et al., Diabetes, 32, 830–838 (1983).

*Primary Examiner*—Robert Gerstl
*Attorney, Agent, or Firm*—Walter Patton

[57] ABSTRACT

This invention relates to novel [(substituted naphthalenyl)alkyl]-3H-1,2,3,5-oxathiadiazole 2-oxides, to the processes for their preparation, to methods for using the compounds, and to pharmaceutical compositions thereof. The compounds have pharmaceutical properties which render them beneficial for the treatment of diabetes mellitus and associated conditions.

27 Claims, No Drawings

NOVEL NAPHTHALENYLALKYL-3H-1,2,3,5-OXATHIADIAZOLE 2-OXIDES USEFUL AS ANTIHYPERGLYCEMIC AGENTS

BACKGROUND OF THE INVENTION

This invention relates to novel [(substituted naphthalenyl)alkyl]-3H-1,2,3,5-oxathiadiazole 2-oxides, to the processes for their preparation, to methods for using the compounds, and to pharmaceutical compositions thereof. The compounds have pharmaceutical properties which render them beneficial for the treatment of diabetes mellitus and associated conditions.

The serious complications of diabetes mellitus such as nephropathy, retinopathy, neuropathy and cataract are all associated with an excessive amount of blood glucose. The major therapeutic objective is therefore the normalization of blood glucose, both in the fasting and postprandial situations.

The therapeutic approaches to the treatment of Non-Insulin Dependent Diabetes Mellitus (NIDDM, Type II) involve the use of diet, insulin or orally active hypoglycemic agents. Presently, such orally active hypoglycemic agents are chosen (a) from sulfonylureas such as chloropropamide, glyburide and others or (b) biguanides such as metformin and related products. Both these groups of agents have serious disadvantages. Sulfonylureas, upon chronic use, lose their effectiveness. In contrast, biguanides suffer from a serious side effect, lactic-acidosis.

More recently, oxazolidinedione (U.S. Pat. No. 4,342,771) and thiazolidinedione (European patent application No. 117,035) derivatives have been described as useful hypoglycemic agents. U.S. Pat. No. 4,461,902 discloses substituted 5-[(4-cyclohexyl-methoxyphenyl)-methyl]thiazolidine-2,4-diones of formula

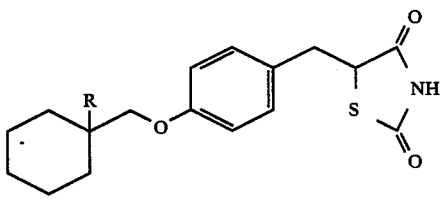

wherein R is methyl (ciglitazone) and related analogues as hypoglycemic agents.

This invention relates to [(substituted naphthalenyl)alkyl]-3H-1,2,3,5-oxathiadiazole 2-oxides of the general formula:

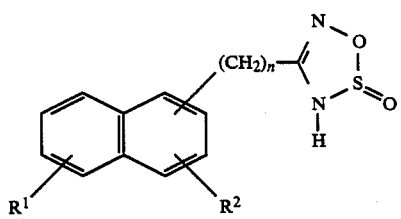

wherein $R^1$ and $R^2$ are independently hydrogen, lower alkyl containing 1 to 6 carbon atoms, alkoxy containing 1 to 6 carbon atoms, halogen, ethynyl, nitrile, methylthio, trifluoromethyl, vinyl, nitro or halogen substituted benzyloxy; n is 0 to 4 and the pharmaceutically acceptable salts thereof having utility as antidiabetic agents, methods for their production and use and pharmaceutical compositions containing them.

The preferred compounds are those of formula (II)

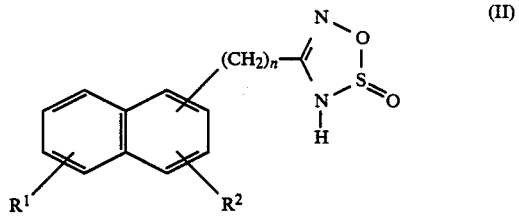

wherein $R^1$ and $R^2$ are independently hydrogen, lower alkyl containing 1 to 6 carbon atoms, alkoxy containing 1 to 6 carbon atoms, halogen, ethynyl, nitrile, trifluoromethyl, vinyl or nitro; n is 1 or 2 and the pharmaceutically acceptable salts thereof.

The oxathiadiazole 2-oxide portion of the compounds of the present invention can exist in more than one tautomeric form. For clarity, only one of the tautomers is represented in the generic formulas (I) and (II) above. The possible tautomeric forms are listed below:

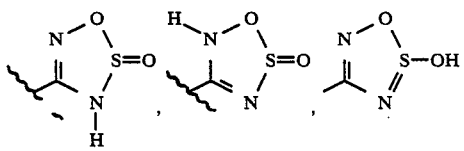

All of said tautomers are included in the present invention. The actual tautomeric form which the compounds of the present invention assume is not known.

This invention also includes mixtures of optically active isomers or partially or completely resolved isomers of the compounds disclosed.

The compounds of this invention are useful as antidiabetic agents for the reduction of blood/plasma sugar levels and for the treatment and/or prevention of diabetic complications and as antihyperlipidemic and antihyperinsulinemic agents.

The most preferred compounds of the present invention are:
4-[(8-bromo-2-naphthalenyl)methyl]-3H-1,2,3,5-oxathiadiazole 2-oxide;
4-[(5-bromo-2-naphthalenyl)methyl]-3H-1,2,3,5-oxathiadiazole 2-oxide;
4-[(3-methyl-2-naphthalenyl)methyl]-3H-1,2,3,5-oxathiadiazole 2-oxide;
4-[2-(5-bromo-2-naphthalenyl)ethyl]-3H-1,2,3,5-oxathiadiazole 2-oxide;
4-[(5-chloro-2-naphthalenyl)methyl]-3H-1,2,3,5-oxathiadiazole 2-oxide;
4-[(1-methyl-2-naphthalenyl)methyl]-3H-1,2,3,5-oxathiadiazole 2-oxide;
4-[(5-ethynyl-2-naphthalenyl)methyl]-3H-1,2,3,5-oxathiadiazole 2-oxide;
4-[(4-bromo-1-methoxy-2-naphthalenyl)methyl]-3H-1,2,3,5-oxathiadiazole 2-oxide;
4-[(4-chloro-1-methoxy-2-naphthalenyl)methyl]-3H-1,2,3,5-oxathiadiazole 2-oxide;
4-[(3-methoxy-2-naphthalenyl)methyl]-3H-1,2,3,5-oxathiadiazole 2-oxide;
4-[(8-chloro-2-naphthalenyl)methyl]-3H-1,2,3,5-oxathiadiazole 2-oxide;

4-[(3-chloro-2-naphthalenyl)methyl]-3H-1,2,3,5-oxa-thiadiazole 2-oxide;

4-[(1-bromo-2-naphthalenyl)methyl]-3H-1,2,3,5-oxa-thiadiazole 2-oxide;

4-[(1-methoxy-2-naphthalenyl)methyl]-3H-1,2,3,5-oxa-thiadiazole 2-oxide;

4-[(1-fluoro-2-naphthalenyl)methyl]-3H-1,2,3,5-oxa-thiadiazole 2-oxide;

4-[(5-methyl-2-naphthalenyl)methyl]-3H-1,2,3,5-oxa-thiadiazole 2-oxide;

4-[(1-bromo-3-methyl-2-naphthalenyl)methyl]-3H-1,2,3,5-oxathiadiazole 2-oxide;

4-[[3-(trifluoromethyl)-2-naphthalenyl]methyl]-3H-1,2,3,5-oxathiadiazole 2-oxide;

4-[[5-(trifluoromethyl)-2-naphthalenyl]methyl]-3H-1,2,3,5-oxathiadiazole 2-oxide;

4-[(1-chloro-2-naphthalenyl)methyl]-3H-1,2,3,5-oxa-thiadiazole 2-oxide;

4-[(1-nitro-2-naphthalenyl)methyl]-3H-1,2,3,5-oxa-thiadiazole 2-oxide;

4-[(8-bromo-1-naphthalenyl)methyl]-3H-1,2,3,5-oxa-thiadiazole 2-oxide;

4-[(3-bromo-4-methoxy-1-naphthalenyl)methyl]-3H-1,2,3,5-oxathiadiazole 2-oxide;

and the pharmaceutically acceptable salts thereof.

DETAILED DESCRIPTION OF THE INVENTION

The naphthalenylalkyl-3H-1,2,3,5-oxathiadiazole 2-oxides of this invention may be administered to mammals, for example, man, cattle or rabbits, either alone or in dosage forms, i.e., capsules or tablets, combined with pharmacologically acceptable excipients.

The compounds of this invention may be given orally. However, the method of administering the present active ingredients of this invention is not to be construed as limited to a particular mode of administration. For example, the compounds may be administered orally in solid form containing such excipients as starch, milk, sugar, certain types of clay and so forth. They may also be administered orally in the form of solutions or they may be injected parenterally. For parenteral administration, they may be used in the form of a sterile solution, preferably of pH 7.2–7.6, containing a pharmaceutically acceptable buffer.

The dosage of the naphthalenylalkyl-3H-1,2,3,5-oxathiadiazole 2-oxides will vary with the form of administration and the particular compound chosen. Furthermore, it will vary with the particular host under treatment. Generally, treatment is initiated with small dosages substantially less than the optimal dose of the compound. Thereafter, the dosage is increased by small increments until efficacy is obtained. In general, the compounds of this invention are most desirably administered at a concentration level that will generally afford effective results without causing any harmful or deleterious side effects.

For oral administration (or as a suppository) to an adult patient, a preferred level of dosage ranges from about 0.01 to 10 mg/kg body weight/day. For parenteral administration to an adult patient, a preferred level of dosage ranges from about 0.005 to 10 mg/kg body weight/day, once daily or divided into 2 to 4 times a week.

Unit dosage forms such as capsules, tablets, pills and the like may contain from about 5.0 mg to about 250 mg of the active ingredients of this invention with a pharmaceutical carrier. Thus, for oral administration, capsules can contain from between about 5.0 mg to about 250 mg of the active ingredients of this invention with or without a pharmaceutical diluent. Tablets, either effervescent or noneffervescent, can contain between about 5.0 to 250 mg of the active ingredients of this invention together with conventional pharmaceutical carriers. Thus, tablets, which may be coated and either effervescent or noneffervescent, may be prepared according to the known art. Inert diluents or carriers, for example, magnesium carbonate or lactose, can be used together with conventional disintegrating agents, for example, magnesium stearate.

The naphthalenylalkyl-3H-1,2,3,5-oxathiadiazole 2-oxides can also be used in combination with dietary restriction, insulin, sulfonylureas, such as chloropropamide and glyburide, biguanides, such as metformin, aldose reductase inhibitors or hypolipidemic agents to produce a beneficial effect in the treatment of diabetes mellitus. In this instance, commercially available insulin preparations or agents exemplified above are suitable. The compounds hereof can be administered sequentially or simultaneously with insulin or the above exemplified agents. Suitable methods of administration, compositions and doses of the insulin preparations or the above exemplified agents are described in medical textbooks; for instance, "Physicians' Desk Reference", 36 ed., Medical Economics Co., Oradell, N.J., U.S.A., 1982.

The compounds of the present invention are prepared according to the general sequence outlined in Scheme I below:

Scheme I

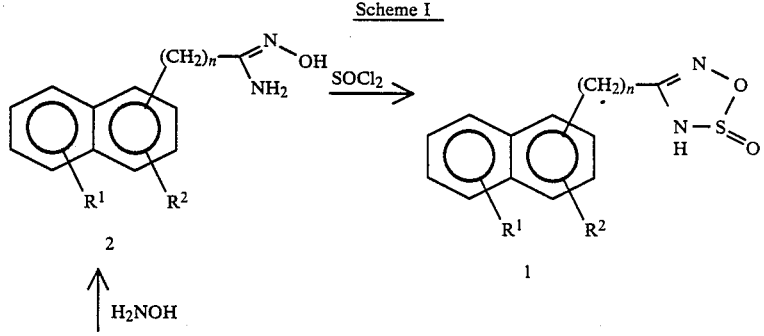

Scheme I

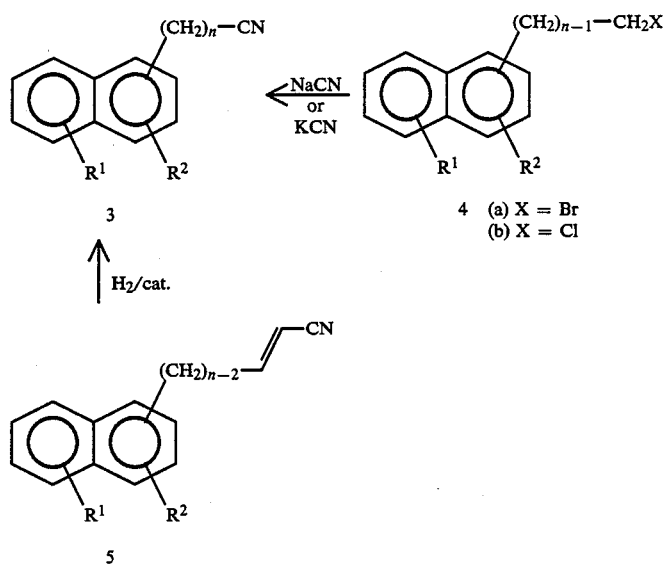

wherein R$^1$, R$^2$, and n are as defined above.

All of the oxathiadiazoles 1, are prepared from the corresponding amidoximes 2, by treatment with thionyl chloride by one of two possible methods, either in the presence of an amine base, such as pyridine or triethylamine, at low temperatures (−23° to 5° C.), or in the absence of base at temperatures from ambient to 110° C. When an amine base is used, the reaction is generally performed in inert organic solvents such as methylene chloride, acetonitrile, or tetrahydrofuran. In the absence of base, higher boiling organic solvents such as benzene or toluene are used. Reaction time ranges from a few minutes to several hours. The oxathiadiazoles are isolated either by concentration of the reaction mixture or by first washing the reaction mixture with water, separating the organic layer and drying before concentrating. Purification is effected either by chromatography on silica gel or recrystallization.

The intermediate amidoximes 2, also have activity as antidiabetic agents. They can exist as either the E or Z isomer, although the Z isomer usually predominates and is more stable. In general, the amidoximes are used without attempting to separate the isomers. The amidoximes are prepared by treatment of the corresponding nitriles 3, with hydroxylamine, the free base of which is liberated from the hydrochloride salt with either sodium methoxide, sodium ethoxide or sodium hydroxide. The reaction is performed in methanol, ethanol or aqueous DMSO at temperatures ranging from ambient to reflux. The amidoximes can be isolated from the reaction mixture either by precipitation via addition of water and subsequent filtration, or by extraction into an organic solvent following removal in vacuo of the reaction solvent. Purification is effected by chromatography on silica gel or recrystallization.

The nitriles 3, required for conversion to the amidoximes, are prepared by one of two general methods; either via catalytic hydrogenation of the α,β-unsaturated nitriles 5, or from the corresponding bromides 4a, or chlorides 4b, by addition of either sodium or potassium cyanide. The addition of cyanide is performed in either ethanol, aqueous acetonitrile or aqueous DMSO from ambient temperature to reflux. The nitriles are isolated by removal of the reaction solvent, followed by partitioning between water and a low boiling organic solvent such as methylene chloride. When DMSO is utilized for the reaction, excess water is added to precipitate the desired product which is collected by filtration. Purification can be effected by chromatography or recrystallization.

Bromide and chloride intermediates 4a and 4b, utilized in the preparation of the above nitriles 3, can be synthesized by various routes as described in Scheme II. Bromides 4a, can be obtained by bromination of alkylnaphthalenes 6, with NBS in an inert organic solvent such as carbon tetrachloride at temperatures ranging from ambient to reflux. The succinimide by-product is removed by filtration and the desired bromides collected upon concentration of the filtrate. Generally bromides 4a prepared from this procedure are used without further purification.

If not commercially available, alkylnaphthalenes 6, can be synthesized starting with phenylacetic acids 10, which are converted to the corresponding phenylacetyl chlorides 9, upon treatment with thionyl chloride. The phenylacetyl chlorides 9, can be treated with ethylene under Lewis-acid conditions to give tetrahydronaphthalene ketones 8. Ketones 8, are treated with methyllithium or methylmagnesium chloride and a Lewis-acid to give alcohols 7, which are aromatized with triphenylmethanol under acidic conditions to the desired naphthalenes 6.

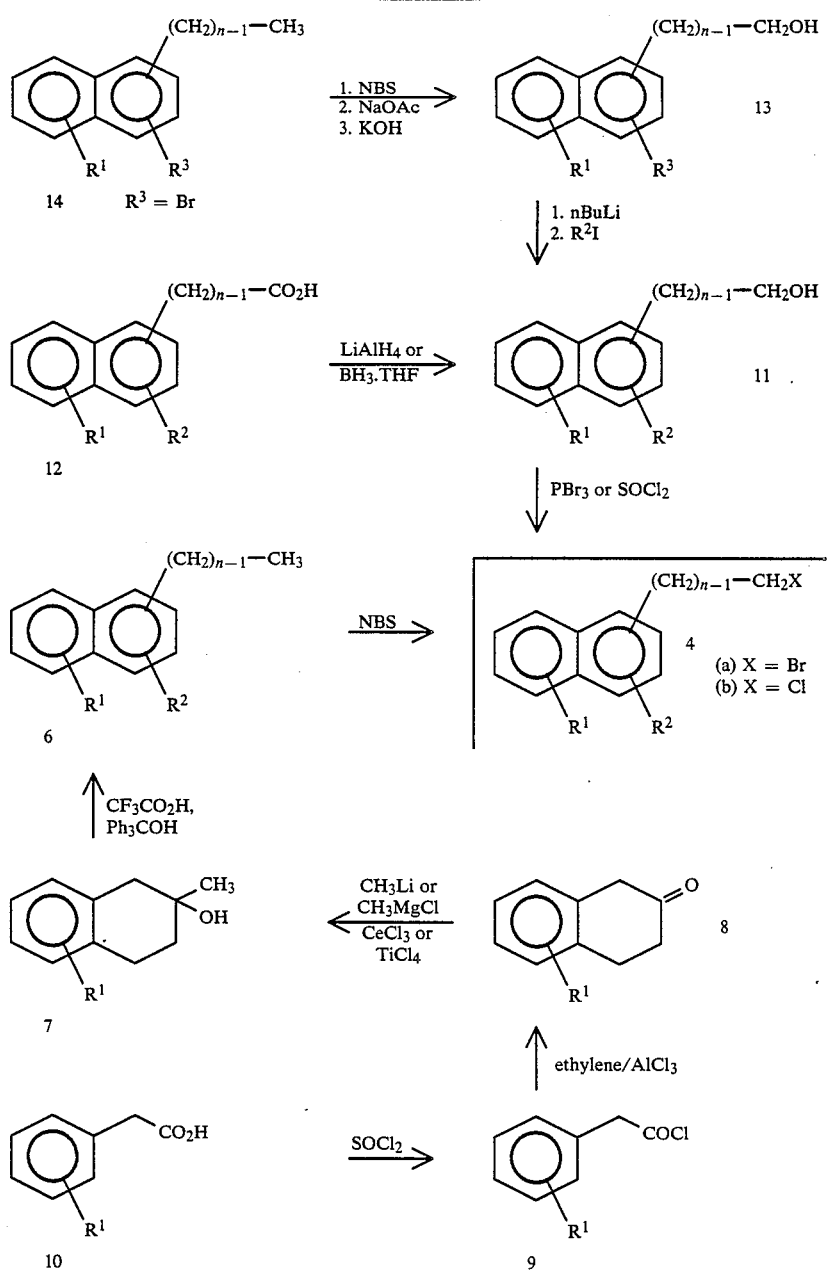

Scheme II

Alternatively, bromides 4a, and chlorides 4b, are obtained by treatment of the corresponding alcohols 11, with a variety of brominating and chlorinating agents such as phosphorous tribromide or thionyl chloride in inert organic solvents. The necessary alcohols 11, are obtained either by reduction of the corresponding acids 12, with diborane or lithium aluminum hydride, or via elaboration of bromomethylnaphthalenes 14. This is accomplished first by conversion to alcohols 13 by bromination of the methyl substituent with a reagent such as N-bromosuccinimide, followed by treatment with sodium acetate and subsequent hydrolysis of the resulting acetates with potassium hydroxide. Bromonaphthalene methanols 13, are then converted to alcohols 11 via lithium halogen exchange with an alkyllithium at low temperature, such as −78° C., in an ethereal solvent, followed by addition of an electrophile such as iodomethane.

As outlined in Scheme III, unsaturated nitriles 5, can be synthesized by treatment of aldehydes 15 with phosphorane 16. The aldehydes 15 are obtained either by reduction of corresponding nitriles 17 or by oxidation of alcohols 18.

Scheme III

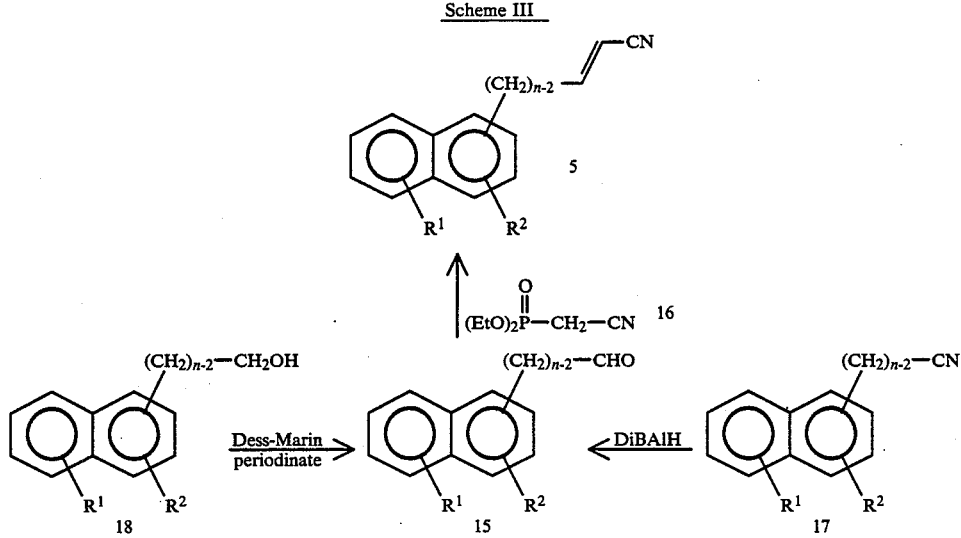

The preferred process for the production of the compounds of the present invention is illustrated by the production of 4-[(5-chloro-2-naphthalenyl)methyl]-3H-1,2,3,5-oxathiadiazole 2-oxide set forth in Scheme IV.

A still further preferred process for the production of the compounds of the present invention is illustrated by the production of 4-[(8-bromo-2-naphthalenyl)methyl]-3H-1,2,3,5-oxathiazole 2-oxide set forth in Scheme V.

Scheme IV

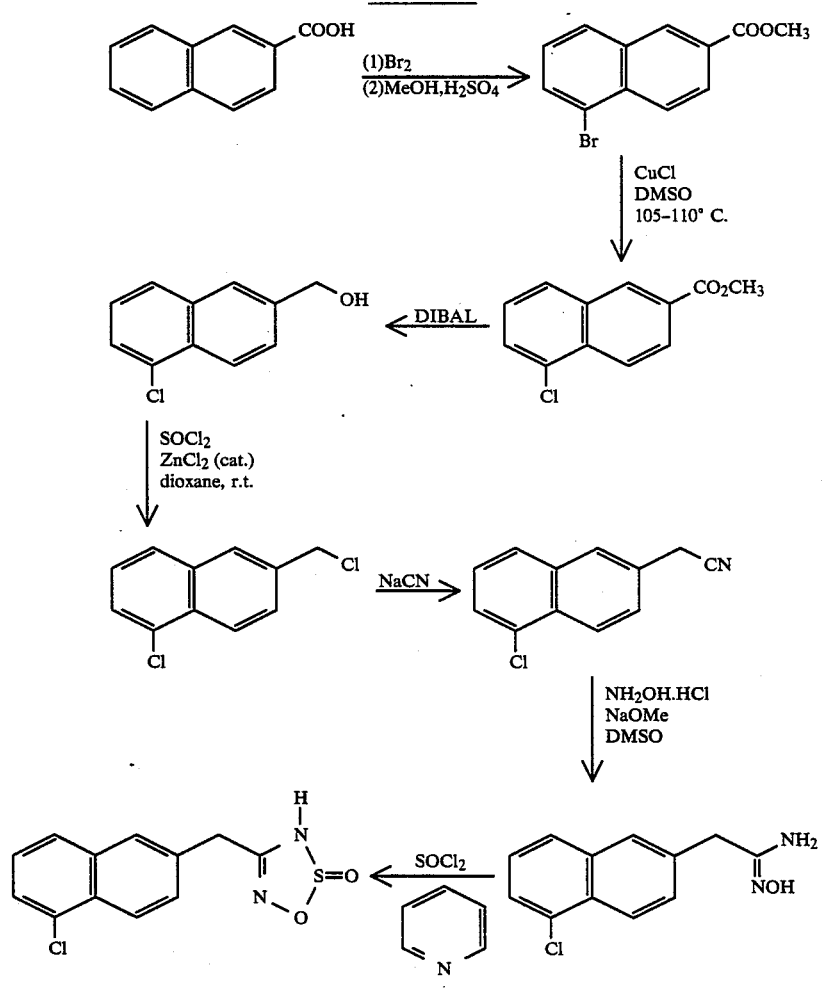

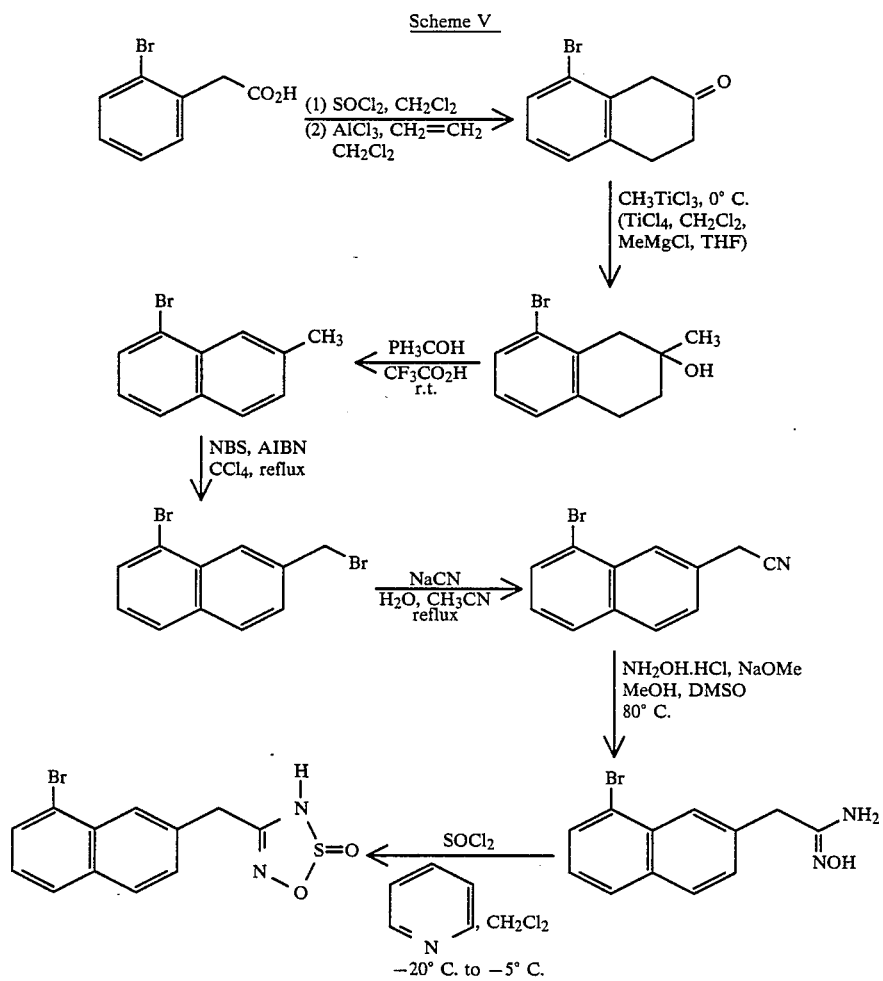

The chemical bases which are used as reagents in this invention to prepare the aforementioned pharmaceutically acceptable salts are those which form non-toxic salts with the various herein described naphthalenylalkyl-3H-1,2,3,5-oxathiadiazole 2-oxides. These particular non-toxic base salts are of such a nature that their cations are said to be essentially non-toxic in character over the wide range of dosage administered. Examples of such cations include those of sodium, potassium, calcium and magnesium. These salts may be prepared by mixing organic solutions of the naphthalenyl alkyl-3H-1,2,3,5-oxathiadiazole 2-oxides in alcohol and the desired alkali metal alkoxide together and then isolating the resulting salts by removal of the solvent and filtration with a non-polar solvent. Stoichiometric quantities of reagents must be employed in order to ensure completeness of reaction and maximum production yields with respect to the desired final product.

The following examples further illustrate the present invention.

EXAMPLE 1

4-[(8-Bromo-2-naphthalenyl)methyl]-3H-1,2,3,5-oxathiadiazole 2-Oxide

Step (1)

Preparation of Ethyl 8-Amino-2-naphthoate

According to the procedure of W. Adcock, et al. *Aust. J. Chem.* 18, 1351 (1965), a suspension of ethyl 8-nitro-2-naphthoate (8.2 g, 0.033 mol) in ethanol (240 mL) was hydrogenated at 50 psi over 10% Pd/C (820 mg) for 4 hours. The mixture was filtered through Solka floc ® and concentrated. Recrystallization of the residue from EtOH/H$_2$O gave a yellow solid (5.2 g, 72%), m.p. 97°-98° C.

NMR (CDCl$_3$, 200 MHz): δ1.44 (t, J=7.3 Hz, 3H), 4.35 (br s, 2H), 4.44 (q, J=7.3 Hz, 2H), 6.80 (d, J=7.3 Hz, 1H), 7.30 (d, J=7.3 Hz, 1H), 7.39 (dd, J=7.3 Hz, 7.3 Hz, 1H), 7.81 (d, J=8.6 Hz, 1H), 8.03 (d, J=8.6 Hz, 1H), 8.64 (s, 1H).

Step (2)

Preparation of 8-Amino-2-naphthoic Acid

According to the procedure of W. Adcock, et al. *Aust. J. Chem.* 18, 1351 (1965), a mixture of ethyl 8-amino-2-naphthoate (5.2 g, 0.024 mol), 1N NaOH (48 mL, 0.048 mol), and dioxane (50 mL) was stirred at room temperature for 3 hours. The dioxane was removed under reduced pressure, and the aqueous phase was diluted with H$_2$O (100 mL) and extracted with ether. Neutralization with acetic acid produced a yellow precipitate which was collected by filtration (3.2 g, 71%), m.p. 221°-223° C.

NMR (DMSO-d$_6$, 200 MHz): δ6.05 (br s, 2H), 6.72 (d, J=7.9 Hz, 1H), 7.09 (d, J=7.9 Hz, 1H), 7.31 (dd, J=7.9

Hz, 7.9 Hz, 1H), 7.76 (d, J=8.8 Hz, 1H), 7.85 (d, J=8.8 Hz, 1H), 8.78 (s, 1H).

Step (3)

Preparation of 8-Bromo-2-naphthoic Acid

According to the procedure of W. Adcock, et al. *Aust. J. Chem.* 18, 1351 (1965) and H. H. Hodgson, et al. *J. Chem. Soc.*, 1620 (1933), to a cooled (10° C.), stirred solution of $NaNO_2$ (1.24 g, 0.0179 mol) in $H_2SO_4$ (16.1 mL) and HOAc (14.9 mL) [prepared by adding $NaNO_2$ to cooled (10° C.) $H_2SO_4$, heating to dissolve, recooling, and adding HOAc] was added a solution of 8-amino-2-naphthoic acid (2.80 g, 0.0150 mol) in HOAc (50 mL) over 10 minutes. The resulting solution was added slowly (over 10 minutes) to a heated (60° C.), stirred solution of CuBr (9.44 g, 0.0658 mol) in concentrated HBr (90 mL). The mixture was warmed to 90° C. for 10 minutes, cooled, diluted with $H_2O$ (200 mL) and filtered to give a green solid, 3.4 g. The crude product was combined with similarly prepared material (450 mg) and recrystallized from EtOH to give an off-white solid (2.3 g, 55%), m.p. 265°–266° C.

NMR (DMSO-$d_6$, 400 MHz): δ7.57 (dd, J=8.2 Hz, 7.5 Hz, 1H), 7.98 (dd, J=7.5 Hz, 1.0 Hz, 1H), 8.07 (m, 2H), 8.11 (d, J=8.5 Hz, 1H), 8.79 (s, 1H), 11.67 (br s, 1H),

MS=m/e 250 (95%), 126 (100%).

Step (4)

Preparation of 8-Bromo-2-hydroxymethylnaphthalene

To a cooled (0° C.), stirred suspension of 8-bromo-2-naphthoic acid (2.25 g, 8.96 mmol) in THF (12 mL) was added $BH_3$·THF (1M in THF, 12.5 mL, 12.50 mmol) over 20 minutes. The cooling bath was removed and stirring was continued at room temperature overnight. The mixture was recooled to 0° C. and saturated aqueous $K_2CO_3$ (8 mL) was added. $H_2O$ (10 mL) was added and the mixture was extracted with ether. The combined extracts were washed with saturated aqueous NaCl, dried ($MgSO_4$) and concentrated. The crude product was recrystallized from ether/hexane to give an off-white solid (1.70 g, 80%), m.p. 110°–111° C.

NMR (CDCl$_3$, 200 MHz): δ4.91 (d, J=5.3 Hz, 2H), 7.31 (dd, J=8.0 Hz, 8.0 Hz, 1H), 7.55 (dd, J=8.7 Hz, 1.6 Hz, 1H), 7.82 (m, 3H), 8.19 (s, 1H).

Step (5)

Preparation of 8-Bromo-2-naphthalenylacetonitrile

According to the procedure of A. Mizuno, et al. *Synthesis* 1007 (1980), a mixture of 8-bromo-2-hydroxymethylnaphthalene (1.70 g, 7.17 mmol), KCN (0.93 g, 14.34 mmol) and 18-crown-6 (0.19 g, 0.72 mmol) in acetonitrile (24 mL) was stirred at room temperature for 15 minutes. A mixture of n-Bu$_3$P (1.60 g, 7.89 mmol) and acetonitrile (7 mL) was added. The mixture was cooled to 0° C., and a solution of CCl$_4$ (1.21 g, 7.89 mmol) in acetonitrile (7 mL) was added. The resulting mixture was stirred at room temperature for two days. Ether (300 mL) was added and the mixture was washed with 10% aqueous citric acid (150 mL). CCl$_4$ (20 mL) was added and the mixture was washed with H$_2$O (2×150 mL); saturated aqueous NaCl (150 mL), dried (MgSO$_4$), and concentrated. The crude material was purified by flash chromatography (eluant EtOAc/hexane (5:95), to EtOAc/hexane (20:80)) to give a yellow solid (1.13 g, 64%), m.p. 55°–56° C.

NMR (CDCl$_3$, 200 MHz): δ3.96 (s, 2H), 7.35 (dd, J=8.3 Hz, 7.2 Hz, 1H), 7.48 (dd, J=8.6 Hz, 2.0 Hz, 1H), 7.83 (m, 3H), 8.18 (d, J=1.2 Hz, 1H),
IR(CCl$_4$, cm$^{-1}$): 2255 (CN).

Step (6)

Preparation of N'-Hydroxy-2-(8-bromonaphthalenyl)ethanimidamide

A mixture of NaOMe (25 wt % in MeOH, 1.6 ml, 6.83 mmol), MeOH (3 mL), and hydroxylamine hydrochloride (0.47 g, 6.83 mmol) was heated for 30 minutes. 8-Bromo-2-naphthalenylacetonitrile (1.12 g, 4.55 mmol) and MeOH (5 mL) were added and heating was continued for 24 hours. The mixture was concentrated, and suspended in H$_2$O (40 mL) and ether (2 mL). The off-white solid was collected by filtration and triturated with ether to give the title compound (790 mg, 62%), m.p. 123°–125° C.

NMR (DMSO-$d_6$, 200 MHz): δ3.50 (s, 2H), 5.50 (s, 2H), 7.38 (dd, J=7.6 Hz, 7.6 Hz, 1H), 7.54 (d, J=8.3 Hz, 1H), 7.85 (d, J=7.6 Hz, 1H), 7.89 (m, 2H), 8.02 (s, 1H), 8.96 (s, 1H).

Step (7)

Preparation of 4-[(8-Bromo-2-naphthalenyl)methyl]-3H-1,2,3,5-oxathiadiazole 2-Oxide To a cooled (0° C.), stirred suspension of N'-hydroxy-2-(8-bromonaphthalenyl)ethanimidamide (437 mg, 1.56 mmol) in pyridine (248 mg, 3.13 mmol) and CH$_2$Cl$_2$ (2 mL) was added thionyl chloride (205 mg, 1.72 mmol). The resulting solution was stirred for 20 minutes, concentrated, and partitioned between ether and water. The organic phase was dried (MgSO$_4$) and concentrated. The product was recrystallized from ethanol/ether to give a white solid (123 mg, 24%), m.p. 157°–158° C.

NMR (DMSO-$d_6$, 400 MHz): δ4.20 (s, 2H), 7.43 (m, 1H), 7.52 (dd, J=8.4 Hz, 1.6 Hz, 1H), 7.89 (dd, J=7.6 Hz, 0.9 Hz, 1H), 7.97 (d, J=8.4 Hz, 1H), 7.99 (d, J=8.4 Hz, 1H), 8.10 (s, 1H), 11.53 (br s, 1H)
IR (KBr, cm$^{-1}$): 3450 (NH),
MS: m/e 324 (17%), 139 (100%),
Anal. Calcd for C$_{12}$H$_9$BrN$_2$O$_2$S: C, 44.32; H, 2.79; N, 8.61%;
Found: C, 44.01; H, 2.60; N, 8.62%.

The compound 4-[(8-bromo-2-naphthalenyl)methyl]-3H-1,2,3,5-oxathiadiazole 2-oxide may also be prepared by the following alternate process.

Step (1)

Preparation of 8-Bromo-2-tetralone

According to the procedure of A. Rosowsky, et al. *J. Org. Chem.* 26, 4232 (1961), to a stirred solution of 2-bromophenylacetic acid (150.0 g, 0.698 mol) in CH$_2$Cl$_2$ (500 mL) was added DMF (1 mL) and thionyl chloride (102 mL, 1.395 mol). The mixture was left standing for 18 hours, concentrated, and azeotroped with CCl$_4$ (3×100 mL). To a cooled (−20° C.) mechanically stirred suspension of AlCl$_3$ (186.0 g, 1.395 mol) in CH$_2$Cl$_2$ (1000 mL) was added a solution of 2-bromophenylacetyl chloride (163 g, 0.698 mol) in CH$_2$Cl$_2$ (350 mL) over 30 minutes. Ethylene was bubbled into the mixture for 1 hour (at −15° C. for 45 minutes then at −10° C. for 15 minutes, total ethylene used: 69.2 g). Stirring at −10° C. was continued for 15 minutes and the mixture was poured onto ice (1200 g). The layers were separated and the organic phase was washed with $H_2O$, saturated aqueous $NaHCO_3$, brine, dried ($MgSO_4$) and concentrated. The resulting yellow solid was taken up in $CH_3CN$ (1000 mL), washed with pentane (2×500 mL) to remove polyethylene, and concentrated to give a yellow solid (146.2 g, 93%). An analytical sample was obtained by recrystallization from ether/hexane.

8-Bromo-2-tetralone is not stable in solution and should be stored cold under $N_2$.

NMR (DMSO-$d_6$, 400 MHz): δ2.48 (t, J=6.6 Hz, 2H), 3.06 (t, J=6.6 Hz, 2H), 3.60 (s, 2H), 7.15 (dd, J=7.6 Hz, 7.6 Hz, 1H), 7.29 (d, J=7.6 Hz, 1H), 7.50 (d, J=7.6 Hz, 1H)

IR (KBr, cm$^{-1}$): 1710 (C=O)

MS: m/e 224 (M+)

Anal. Calcd for $C_{10}H_9BrO$: C, 53.36; H, 4.03%; Found: C, 53.18, H, 3.74%.

Step (2)

Preparation of 8-Bromo-2-hydroxy-2-methyl-1,2,3,4-tetrahydronaphthalene

According to the procedure of M. T. Reetz, et al., *Tetrahedron* 42, (11), 2931 (1986), to a cooled (−30° C.) stirred solution of $TiCl_4$ (109.9 g, 0.580 mol) in $CH_2Cl_2$ (580 mL) was added 3.0 M $CH_3MgCl$/THF (193 mL, 0.580 mol) over 35 minutes. To the resulting dark purple mixture was added a solution of 8-bromo-2-tetralone (108.7 g, 0.483 mol) in $CH_2Cl_2$ (150 mL) over 30 minutes. The mixture was warmed to 0° C. After 2 hours, the mixture was poured onto ice (1000 g). The layers were separated, and the organic phase was washed with 2N HCl, brine, dried ($MgSO_4$), and concentrated to give a brown solid (117.0 g, 100%). This material was used directly in the next reaction without further purification. An analytical sample was prepared from 300 mg of previously prepared material by recrystallization from hexane, m.p. 73°-74° C.

NMR (DMSO-$d_6$, 400 MHz): δ1.24 (s, 3H), 1.58 (m, 1H), 1.70 (m, 1H), 2.57 (d, J=17.0 Hz, 1H), 2.64 (m, 1H), 2.70 (d, J=17.0 Hz, 1H), 2.95 (m, 1H), 4.48 (s, 1H), 7.03 (dd, J=7.6 Hz, 7.6 Hz, 1H), 7.11 (d, J=7.6 Hz, 1H), 7.39 (d, J=7.6 Hz, 1H)

IR (KBr, cm$^{-1}$): 3350 (OH),

MS: m/e 240 (M+), 222 (M+−$H_2O$)

Anal. Calcd for $C_{11}H_{13}BrO$: C, 54.79; H, 5.43%; Found: C, 54.43; H, 5.39%.

Step (3)

Preparation of 1-Bromo-7-methylnaphthalene

According to the procedure of H. Fu, et al., *Tetrahedron Lett.* 3217 (1974), a mixture of triphenylmethanol (138.2 g, 0.531 mol), 8-bromo-2-hydroxy-2-methyl-1,2,3,4-tetrahydronaphthalene (116.4 g, 0.483 mol), and trifluoroacetic acid (338 mL) was stirred at room temperature for 2 days. The mixture was extracted with hexane (500 mL and 250 mL). The combined extracts were washed with $H_2O$ (2×500 mL), saturated aqueous $NaHCO_3$ (500 mL), brine (500 mL), dried ($MgSO_4$), and concentrated to about 200 mL. This solution was left standing until the triphenylmethane crystallized. After filtration, the filtrate was concentrated and purified by flash chromatography ($SiO_2$, eluant:hexane) to give a colorless oil (72.2 g, 70%). An analytical sample was obtained from 200 mg of similarly prepared material by Kugelrohr distillation.

NMR (DMSO-$d_6$, 400 MHz): δ2.53 (s, 3H), 7.36 (m, 1H), 7.46 (dd, $J_1$=8.6 Hz, $J_2$=1.0 Hz, 1H), 7.83 (dd, $J_1$=7.4 Hz, $J_2$=1.0 Hz, 1H), 7.91 (m, 3H)

IR (KBr, cm$^{-1}$): 3050 (CH),

MS: m/e 220 (M+), 141 (M+−Br),

Anal. Calcd for $C_{11}H_9Br$: C, 59.75; H, 4.10%; Found: C, 59.68; H, 4.15%.

Step (4)

Preparation of 8-Bromo-2-bromomethylnaphthalene

To boiling $CCl_4$ (250 mL) was added NBS (20.4 g, 0.114 mol) and AIBN (1.4 g, 0.009 mol). After 1 minute, a solution of 1-bromo-7-methylnaphthalene (24.1 g, 0.109 mol) in $CCl_4$ (15 mL) was added all at once. Within 1 minute, the reaction became quite exothermic and the heating mantle was removed for several minutes. Heating was resumed for 30 minutes. The mixture was cooled, filtered, and the filtrate was concentrated to give an off-white solid (32.7 g). The product was combined with similarly prepared material (32.6 g) and recrystallized from ethyl acetate/hexane to give the product (29.6 g, 45%).

NMR (DMSO-$d_6$, 300 MHz): δ4.99 (s, 2H), 7.48 (m, 1H), 7.68 (dd, J=8.7 Hz, 1.8 Hz, 1H), 7.93 (dd, J=7.5 Hz, 0.9 Hz, 1H), 8.00 (d, J=7.8 Hz, 1H), 8.03 (d, J=8.7 Hz, 1H), 8.23 (s, 1H).

Step (5)

Preparation of 8-Bromo-2-naphthalenylacetonitrile

To a stirred partial solution of 8-bromo-2-bromomethylnaphthalene (29.6 g, 0.0987 mol) in acetonitrile (180 mL) was added a solution of NaCN (5.8 g, 0.118 mol) in $H_2O$ (20 mL). The resulting mixture was heated under reflux for 1 hour 20 minutes. The mixture was cooled, concentrated, and partitioned between ether and $H_2O$. The organic phase was washed with $H_2O$, saturated aqueous $NaHCO_3$, brine, dried ($MgSO_4$), and concentrated to give a pale yellow solid (24.1 g, 99%). An analytical sample was obtained by recrystallization of 100 mg of similarly prepared material from toluene/hexane, m.p. 56° C.

NMR (DMSO-$d_6$, 400 MHz): δ4.32 (s, 2H), 7.46 (m, 1H), 7.58 (dd, J=8.4 Hz, 1.7 Hz, 1H), 7.92 (dd, J=7.5 Hz, 1.0 Hz, 1H), 8.00 (d, J=8.4 Hz, 1H), 8.04 (d, J=8.4 Hz, 1H), 8.14 (s, 1H)

IR (KBr, cm$^{-1}$): 2250 (CN);

MS: m/e 245 (M+), 166 (M+−Br),

Anal. Calcd for $C_{12}H_8BrN$: C, 58.56; H, 3.28; N, 5.69%; Found: C, 58.69; H, 3.28; N, 5.51%.

Step (6)

Preparation of N'-Hydroxy-2-(8-bromonaphthalenyl)ethanimidamide

To a stirred solution of 8-bromo-2-naphthalenylacetonitrile (24.1 g, 0.0979 mol) and hydroxylamine hydrochloride (13.6 g, 0.196 mol) in DMSO (150 mL) was added NaOMe (25 wt % in MeOH; 4.48 mL, 0.196 mol). The resulting mixture was heated to 80° C. for 1 hour 30 minutes. The MeOH was removed by rotary evaporation and $H_2O$ (400 mL) was added to the remaining mixture. After 30 minutes, the resulting solid was collected by filtration and recrystallized from toluene to give a white solid (20.8 g, 76%). An analytical sample was obtained from previously prepared material by recrystallization from toluene, m.p. 121°-122° C.

NMR (DMSO-d$_6$, 400 MHz): δ3.50 (s, 2H), 5.54 (br s, 2H), 7.38 (m, 1H), 7.54 (dd, J=8.4 Hz, 1.5 Hz, 1H), 7.85 (dd, J=7.4 Hz, 0.8 Hz, 1H), 7.93 (m, 2H), 8.03 (s, 1H), 8.98 (s, 1H)

IR (KBr, cm$^{-1}$): 3440, 3300 (NH and OH), 1650 (C=N),

MS: m/e 278 (M+),

Anal. Calcd for C$_{12}$H$_{11}$BrN$_2$O: C, 51.63; H, 3.97; N, 10.03%;

Found: C, 51.56; H, 3.90; N, 9.79%.

Step (7)

Preparation of 4-[(8-Bromo-2-naphthalenyl)methyl]-3H-1,2,3,5-oxathiadiazole 2-Oxide To a cooled (−20° C.) stirred suspension of N'-hydroxy-2-(8-bromonaphthalenyl)ethanimidamide (20.8 g, 0.0745 mol) in pyridine (12.0 mL, 0.149 mol) and CH$_2$Cl$_2$ (75 mL) was added a solution of thionyl chloride (5.7 mL, 0.783 mol) in CH$_2$Cl$_2$ (25 mL) over 10 minutes. The mixture was allowed to warm to −5° C. over 40 minutes (all material went into solution). H$_2$O (200 mL) was added and the resulting precipitate was collected by filtration. Recrystallization from ethanol (50 mL) gave an off-white solid (12.7 g, 53%). Analytical data for previously prepared material follows, m.p. 159°–160° C.

NMR (DMSO-d$_6$, 400 MHz): δ4.20 (s, 2H), 7.43 (m, 1H), 7.52 (dd, J=8.4 Hz, 1.6 Hz, 1H), 7.89 (dd, J=7.5 Hz, 0.8 Hz, 1H), 7.97 (d, J=8.4 Hz, 1H), 7.99 (d, J=8.5 Hz, 1H), 8.10 (s, 1H), 11.53 (br s, 1H)

IR (KBr, cm$^{-1}$): 1600 (C=N)

MS: m/e 324 (M+)

Anal. Calcd for C$_{12}$H$_9$BrN$_2$O$_2$S: C, 44.32; H, 2.79; N, 8.61%;

Found: C, 44.10; H, 2.56; N, 8.34%.

Example 2

4-[(5-Chloro-2-naphthalenyl)methyl]-3H-1,2,3,5-oxathiadiazole 2-Oxide

Step (1)

Preparation of Ethyl 5-Amino-2-naphthoate

A suspension of ethyl 5-nitro-2-naphthoate (8.0 g, 0.0326 mol) in EtOH (200 mL) was hydrogenated over 10% Pd/C (600 mg) at 50 psi for 3 hours 30 minutes. The mixture was filtered through Solka floc and concentrated to give a yellow solid (7.0 g, 100%), m.p. 94°–95° C.

NMR (CDCl$_3$, 200 MHz): δ1.44 (t, J=7.4 Hz, 3H), 4.19 (br s, 2H), 4.54 (q, J=7.4 Hz, 2H), 6.87 (dd, J=7.2 Hz, 1.4 Hz, 1H), 7.34 (dd, J=7.2 Hz, 7.2 Hz, 1H), 7.45 (dd, J=7.2 Hz, 1.4 Hz, 1H), 7.85 (d, J=8.9 Hz, 1H), 8.02 (dd, J=8.9 Hz, 2.0 Hz), 8.55 (d, J=2.0 Hz, 1H).

Step (2)

Preparation of 5-Amino-2-naphthoic Acid

A mixture of ethyl 5-amino-2-naphthoate (7.0 g, 0.0325 mol), dioxane (40 ml), and 1 N NaOH (39 mL) was stirred at room temperature for 16 hours. The dioxane was removed under reduced pressure, H$_2$O (50 mL) was added, and the mixture was neutralized with acetic acid (2.23 mL). The resulting brown solid precipitate was collected by filtration to give the desired product (5.4 g, 89%), m.p. 231°–234° C.

NMR (DMSO-d$_6$, 300 MHz): δ6.78 (dd, J=6.9 Hz, 1.5 Hz, 1H), 7.26 (m, 2H), 7.80 (dd, J=9.0 Hz, 1.8 Hz, 1H), 8.14 (d, J=9.0 Hz, 1H), 8.39 (d, J=1.5 Hz, 1H).

Step (3)

Preparation of 5-Chloro-2-naphthoic Acid

According to the procedure of W. Adcock, et al. Aust. J. Chem., 18, 1351 (1965), to a cooled (10° C.), stirred solution of NaNO$_2$ (1.19 g, 0.0173 mol) in H$_2$SO$_4$ (15.6 mL) and HOAc (14.4 mL) [prepared by adding NaNO$_2$ to cooled H$_2$SO$_4$, heating to dissolve, recooling, and adding HOAc] was added a suspension of 5-amino-2-naphthoic acid (2.70 g, 0.0144 mol) in HOAc (48 mL) over 14 minutes. The resulting solution was slowly added (over 15 minutes) to a heated (60° C.) solution of CuCl (6.28 g, 0.0635 mol) in concentrated HCl (88 mL).

Heating was continued for 30 minutes. The mixture was cooled to 5° C., diluted with H$_2$O (200 mL), and filtered to give a gray solid (2.5 g). The material was dissolved in hot EtOH, treated with activated charcoal, and recrystallized to give a white solid (1.15 g, 38%), m.p. 263°–265° C.

NMR (DMSO-d$_6$, 400 MHz): δ7.59 (dd, J=7.5 Hz, 7.5 Hz, 1H), 7.83 (dd, J=7.5 Hz, 1.0 Hz, 1H), 8.13 (dd, J=8.7 Hz, 1.4 Hz, 1H), 8.15 (d, J=8.7 Hz, 1H), 8.25 (d, J=8.7 Hz, 1H), 8.68 (d, J=1.4 Hz, 1H)

MS: m/e 206 (100%), 189 (42%), 161 (42%).

Step (4)

Preparation of 5-Chloro-2-hydroxymethylnaphthalene

To a cooled (0° C.), stirred suspension of 5-chloro-2-naphthoic acid (1.10 g, 5.32 mmol) in THF (10 mL) was added BH$_3$·THF (1M in THF, 7.50 mL, 7.50 mmol) over 10 minutes. The resulting mixture was then heated under reflux for 1 hour 30 minutes, recooled to 0° C., and saturated aqueous K$_2$CO$_3$ (4 mL) was added. H$_2$O (20 mL) was added and the mixture was extracted with ether. The combined extracts were washed with brine, dried (MgSO$_4$), and concentrated to give a pale yellow solid (0.94 g, 97%), m.p. 72°–75° C.

NMR (CDCl$_3$, 200 MHz): δ4.87 (s, 2H), 7.38 (dd, J=7.1 Hz, 7.1 Hz, 1H), 7.58 (m, 2H), 7.75 (d, J=7.9 Hz, 1H), 7.82 (s, 1H), 8.26 (d, J=8.9 Hz, 1H).

Step (5)

Preparation of 5-Chloro-2-chloromethylnaphthalene

A mixture of 5-chloro-2-hydroxymethylnaphthalene (0.93 g, 5.12 mmol), triphenylphosphine (1.48 g, 5.64 mmol), CCl$_4$ (0.87 g, 5.64 mmol), and CH$_2$Cl$_2$ (10 mL) was stirred at room temperature for 2 days, concentrated, and triturated with ether. The filtrate was concentrated to give a pale yellow solid (1.37 g). NMR analysis showed the material to contain triphenylphosphine. The product was used without further purification in the next step.

NMR (DMSO-d$_6$, 300 MHz): δ4.96 (s, 2H), 7.72 (m, 2H), 7.93 (m, 3H), 8.08 (d, J=1.2 Hz, 1H), 8.19 (d, J=9.0 Hz, 1H).

Step (6)

Preparation of 5-Chloro-2-naphthalenylacetonitrile

A mixture of 5-chloro-2-chloromethylnaphthalene (1.37 g crude product, 5.12 mmol), NaCN (0.275 g, 5.61 mmol), CH$_3$CN (10 mL), and H$_2$O (1 mL) was heated under reflux for 5.5 hours, cooled, and stirred at room temperature overnight. The mixture was partitioned between ether and H$_2$O. The aqueous phase was extracted with ether, and the combined ether layers were washed with brine, dried (MgSO$_4$), and concentrated in vacuo. Purification by flash chromatography (eluant EtOAc/hexane (10:90)) gave a pale yellow solid (600 mg, 58%), m.p. 95°-98° C.

NMR (CDCl$_3$, 300 MHz): δ3.91 (s, 2H), 7.41 (m, 2H), 7.73 (d, J=8.1 Hz, 1H), 7.81 (m, 2H), 8.26 (d, J=8.7 Hz, 1H)

IR (CHCl$_3$, cm$^{-1}$): 2260 (CN).

Step (7)

Preparation of N'-Hydroxy-2-(5-chloronaphthalenyl)ethanimidamide

A mixture of NaOMe (25 wt % in MeOH, 1.02 mL, 4.46 mmol), MeOH (4 mL), and hydroxylamine hydrochloride (310 mg, 4.46 mmol) was heated at reflux for 20 minutes. 5-Chloro-2-naphthalenylacetonitrile (600 mg, 2.98 mmol) and additional MeOH (4 mL) were added and heating was continued overnight. Additional hydroxylamine hydrochloride (150 mg, 2.16 mmol) and NaOMe (25 wt % in MeOH, 490 L, 2.14 mmol) were added and heating was resumed for 4 hours. The mixture was cooled, concentrated, and suspended in H$_2$O. The solid was collected by filtration and triturated with ether to give a pale yellow solid (478 mg, 69%), m.p. 121°-125° C.

NMR (DMSO-d$_6$, 300 MHz): δ3.46 (s, 2H), 5.46 (s, 2H), 7.47 (dd, J=7.8 Hz, 7.8 Hz, 1H), 7.60 (m, 2H), 7.86 (m, 2H), 8.08 (d, J=8.7 Hz, 1H), 8.93 (s, 1H).

Step (8)

Preparation of 4-[(5-Chloro-2

Preparation of 4-[(5-Chloro-2-naphthalenyl)methyl]-3H-1,2,3,5-oxathiadiazole 2-Oxide To a cooled (0° C.), stirred suspension of N'-hydroxy-2-(5-chloronaphthalenyl)ethanimidamide (470 mg, 2.00 mmol) in CH$_2$Cl$_2$ (3 mL) and pyridine (325 μL, 4.00 mmol) was added thionyl chloride (160 μL, 2.20 mmol) over 2 minutes. The resulting solution was stirred for 25 minutes. H$_2$O (10 mL) was added and the mixture was extracted with CH$_2$Cl$_2$ (2×25 mL). The combined extracts were dried (MgSO$_4$) and concentrated. Purification by flash chromatography (eluant EtOAc/hexane (20:80)) and recrystallization from ethanol/ether gave off-white needles (88 mg, 16%), m.p. 164°-165° C.

NMR (DMSO-d$_6$, 400 MHz): δ4.16 (s, 2H), 7.52 (dd, J=7.9 Hz, 7.9 Hz, 1H), 7.61 (dd, J=8.7 Hz, 1.7 Hz, 1H), 7.70 (d, J=7.9 Hz, 1H), 7.90 (d, J=7.9 Hz, 1H), 7.94 (s, 1H), 8.16 (d, J=8.7 Hz, 1H), 11.51 (br s, 1H).

MS: m/e 280 (19%), 175 (100%),

Anal. Calcd for C$_{12}$H$_9$ClN$_2$O$_2$S: C, 51.34; H, 3.23; N, 9.98%;

Found: C, 51.26; H, 3.17; N, 9.88%.

EXAMPLE 3

4-[(1-Methyl-2-naphthalenyl)methyl]-3H-1,2,3,5-oxathiadiazole 2-Oxide

Step(1)

Preparation of 1-Bromo-2-bromomethylnaphthalene

According to the procedure of B. Rickborn, et al. J. Org. Chem. 48, 3869 (1983), a mixture of 1bromo-2-melthylnaphthalene (146 g, 0.66 mol) and benzoyl peroxide (1.0 g, 0.004 mol) in CCl$_4$ (600 mL) was heated to reflux and n-bromosuccinimide (131 g, 0.74 mol) was added portionwise over 90 minutes. After the addition was complete, the resulting mixture was maintained at reflux for 2 hours, then cooled to room temperature and a precipitate formed. The solid was removed by filtration and the filtrate was concentrated in vacuo to a volume of 300 mL before storing at 0° C. After 12 to 15 hours, the yellow solid which had crystallized was collected by filtration, washed with CCl$_4$ and dried in vacuo to give the desired product (122.2 g, 62%), of sufficient purity for use in the subsequent reaction.

NMR (DMSO-d$_6$): δ8.23 (d,J=8.4 Hz, 1H), 7.99 (d,J=8.0 Hz; 1H), 7.98 (d,J=8.4 Hz, 1H), 7.71 (m, 1H), 7.70 (d,J=8.4 Hz, 1H), 7.64 (m, 1H), 4.98 (s, 2H)

IR (KBr): 1215, 815, 760 cm$^{-1}$,

MS (EI): 300(M+), 219(100),

Anals. Calcd for C$_{11}$H$_8$Br$_2$: C, 44.04H, 2.69%;

Found: C, 43.98H, 2.60%.

Step (2)

Preparation of 1-Bromo-2naphthalenemethanol Acetate

A mixture of 1-bromo-2-bromomethylnaphthalene (120 g, 0.40 mol) and anhydrous sodium acetate (131.3 g, 1.6 mol) in glacial acetic acid (450 mL) was heated to reflux for a total of 20 hours. The mixture was cooled to room temperature and the solvent removed in vacuo. The residue was partitioned between CH$_2$Cl$_2$ (300 mL), and water (300 mL) and the aqueous layer extracted with CH$_2$Cl$_2$. The combined organic layers were washed with water (3×300 mL), saturated aqueous sodium carbonate (2×200 mL), brine, dried over anhydrous sodium sulfate and concentrated in vacuo. The product (105 g, 94%) was obtained as a yellow solid of sufficient purity for use in the subsequent reaction.

NMR (DMSO-d$_6$): δ8.23 (d,J=8.2 Hz, 1H), 8.00 (d,J=8.5 Hz, 2H), 7.71 (m, 1H), 7.63 (m, 1H), 7.59 (d,J=8.5 Hz, 1H), 5.35 (s, 3H), 2.12 (s, 3H)

IR (KBr): 1745, 1240, 815 cm$^{-1}$

MS (EI): 278(M+), 199(68), 157(100)

Anal. Calcd for C$_{13}$H$_{11}$BrO$_2$: C, 55.94; H, 3.97%;

Found: C, 55.95; H, 3.92%.

Step (3)

Preparation of 1-Bromo-2-naphthalenemethanol

Potassium hydroxide (25.3 g, 0.45 mol) was added to a solution of 1-bromo-2-naphthalenemethanol acetate (105 g, 0.38 mol) in methanol (300 mL) at room temperature. The resulting yellow solution was stirred at room temperature for 3 hours, then diluted with water and a precipitate was formed. The mixture was extracted with ether (2×300 mL), and the combined organic layers were washed with water (250 mL), brine, dried over anhydrous magnesium sulfate and concentrated in vacuo. The pure product was obtained as a light yellow solid (86.8 g, 96%).

NMR (DMSO-d$_6$): δ8.19 (d,J=8.5 Hz, 1H), 7.98 (d,J=8.1 Hz, 1H), 7.96 (d,J=6.9 Hz, 1H), 7.72 (d,J=8.4 Hz, 1H), 7.66 (t,J=7.0 Hz, 1H), 7.57 (t,J=7.0 Hz, 1H), 5.58 (t,J=5.5 Hz, 1H), 4.75 (d,J=5.5 Hz, 2H)

IR (KBr): 3200, 1510, 1330, 1070, 810, 770 cm$^{-1}$,

MS (EI): 236(M+), 157(57), 129(100),

Anal. Calcd for C$_{11}$H$_9$BrO: C, 55.72; H, 3.83%;

Found: C, 55.60; H, 3.77%.

Step (4)

Preparation of 1Methyl-2-naphthalenemethanol

1-Bromo-2-naphthalenemethanol (36.5 g, 154 mmol) was added portionwise to a suspension of sodium hydride (60% dispersion, 7.39 g, 185 mmol, washed 3×20 mL hexanes) in anhydrous THF (800 mL) at 0° C. After the addition was completed (mild evolution of hydrogen) the resulting mixture was stirred at 0° C. 15 minutes, then the ice bath was removed and the mixture stirred at room temperature for 2 hours. The mixture was cooled to −78° C. and treated with n-BuLi (1.6 M in hexanes, 116 mL, 185 mmol) added steadily dropwise over 15 minutes, resulting in a color change from an orange to a green solution. The mixture was stirred at −78° C. 1.5 hours, then treated with iodomethane (65.6 g, 462 mmol) added rapidly and the resulting solution stirred for 1 hour at −78° C. The dry ice bath was removed and the mixture allowed to warm to room temperature over 40 minutes. Water (100 mL) was added to quench the reaction and the mixture poured into saturated ammonium chloride (200 mL) and extracted with ether (3×400 mL). The combined organic layers were washed with water (2×250 mL), brine, dried over anhydrous magnesium sulfate and concentrated in vacuo to give a yellow solid (27 g).

Recrystallization from EtOAc/hexanes (2:8) gave the desired product (16.3 g, 62%) as an off-white crystalline solid.

NMR (DMSO-$d_6$): $\delta$8.07 (d,J=8.5 Hz, 1H), 7.88 (d,J=8.0 Hz, 1H), 7.73 (d,J=8.4 Hz, 1H), 7.56 (d,J=8.4 Hz, 1H), 7.52 (m, 1H), 7.46 (m, 1H), 5.17 (t,J=5.3 Hz, 1H), 4.69 (d,J=5.3 Hz, 2H), 2.57 (s, 3H)

IR (KBr): 3260, 2890, 1390, 1015, 820, 760 cm$^{-1}$,

MS (+EI): 172(M+), 154(100), 128(46),

Anal. Calcd. for $C_{12}H_{12}O$: C, 83.69; H, 7.03%;

Found: C, 83.51; H, 6.86%.

Alternate Step (4)

Preparation of 1-Methyl-2-naphthalenemethanol

A solution of 1-bromo-2-naphthalenemethanol (40.0 g, 169 mmol) in anhydrous THF (600 mL) was cooled to −78° C. and treated with n-BuLi (1.6M in hexanes, 232 mL, 371 mmol) added dropwise from an addition funnel over 30 minutes. After the addition was complete, the resulting mixture was stirred for 0.5 hours at −78° C. and treated with iodomethane (31.5 mL, 71.9 g, 506 mmol) added rapidly. The mixture was stirred for 3 hours at −78° C., then quenched with water and warmed to room temperature. The mixture was poured into 1N HCl (300 mL) and extracted with ether (3×500 mL). The combined organic layers were washed with water (2×200 mL), brine, dried over anhydrous magnesium sulfate and concentrated in vacuo to give a yellow solid (29 g).

The solid was recrystallized from EtOAc/hexanes to give pure product (14.7 g, 51%) as a white crystalline solid.

NMR (DMSO-$d_6$): $\delta$8.07 (d,J=8.5 Hz, 1H), 7.88 (d,J=8.0 Hz, 1H), 7.73 (d,J=8.4 Hz, 1H), 7.56 (d,J=8.4 Hz, 1H), 7.52 (m, 1H), 5.17 (t,J=5.3 Hz, 1H), 4.69 (d,J=5.3 Hz, 2H), 2.57 (s, 3H)

IR (KBr): 3260, 2890, 1390, 1015, 820, 765 cm$^{-1}$,

MS (+EI): 172(M+), 154(100), 128(46)

Anal. Calcd for $C_{12}H_{12}O$: C, 83.69; H, 7.03%;

Found: C, 83.49; H, 6.96%.

Step (5)

Preparation of 2-Bromomethyl-1-methylnaphthalene

Carbon tetrabromide (9.76 g, 29.4 mmol) and triphenylphosphine (7.72 g, 29.4 mmol) were added to a stirred suspension of 1-methyl-2-naphthalene-methanol (4.6 g, 26.7 mmol) in $CH_2Cl_2$ (100 mL) at 0° C. The mixture became a light yellow solution and was stirred at 0° C. for 15 minutes. Additional carbon tetrabromide (0.89 g, 2.67 mmol) and triphenylphoshine (0.70 g, 2.67 mmol) were added and the resulting solution stirred for 5 minutes at 0° C. (Tlc indicated no starting material present.) The solvent was removed in vacuo and the remaining yellow oil triturated with ether (200 mL) to give a precipitate. The solid was removed by filtration and the filtrate concentrated in vacuo.

Flash chromatography on silica gel with elution by EtOAc/hexanes (1:9) gave pure product (5.6 g, 88%) as a white crystalline solid.

NMR (DMSO-$d_6$): $\delta$8.12 (d,J=8.3 Hz, 1H), 7.88 (d,J=7.5 Hz, 1H), 7.75 (d,J=8.4 Hz, 1H), 7.55 (m, 1H), 7.53 (m, 1H), 7.50 (d,J=8.4 Hz, 1H), 4.94 (s, 2H), 2.65 (s, 3H)

IR (KBr): 3450, 1210, 820, 765 cm$^{-1}$,

MS (EI): 234(M+), 155(100)

Step (6)

Preparation of 1-Methyl-2-naphthalenylacetonitrile

KCN (1.52 g, 23.4 mmol) was added to a solution of 2-bromomethyl-1-melthylnaphthalene (5.5 g, 23.4 mmol) in water/$CH_3CN$ (1:9, 100 mL) at room temperature. The resulting mixture was heated to reflux for 1 hour, cooled to room temperature, and concentrated in vacuo. The residue was redissolved in $CH_2Cl_2$ (150 mL), washed with water (2×50 mL), brine, dried over anhydrous sodium sulfate, and solvent removed in vacuo to give the desired product (4.0 g, 67%) as an orange colored solid of sufficient purity for use in the subsequent reaction.

NMR (DMSO-$d_6$): $\delta$8.11 (d,J=8.5 Hz, 1H), 7.90 (d,J=7.7 Hz, 1H), 7.80 (d,J=8.5 Hz, 1H), 7.58 (m, 1H), 7.53 (m, 1H), 7.48 (d,J=8.5 Hz, 1H), 4.20 (s, 2H), 2.62 (s, 3H)

IR (KBr): 3400, 2240, 1390, 820, 755 cm$^{-1}$,

MS (EI): 181 (M+, 100), 166 (53), 141 (69),

Anal. Calcd for $C_{13}H_{11}N$: C, 86.15; H, 6.12; N, 7.73%;

Found: C, 85.43; H, 5.98; N, 7.47%.

Step (7)

Preparation of N'-Hydroxy-2-(1-methylnaphthalenyl)ethanimidamide

Hydroxylamine hydrochloride (5.62 g, 80.8 mmol) was added in one portion to a solution of NaOMe, freshly prepared from sodium (1.86 g, 80.8 mmol) in methanol. The resulting mixture was stirred for 1 hour at room temperature, during which a precipiatate was formed. 1-Methyl-2-naphthalenylacetonitrile (9.75 g, 53.9 mmol) was added in one portion and the resulting mixture heated to reflux a total of 42 hours. The mixture was cooled to room temperature, concentrated in vacuo to approximately 150 mL, and diluted with water (175 mL) to give a precipitate. The mixture was cooled to 0° C. for 10 minutes, the precipitate was collected by filtration, washed with water, followed by EtOAc/hexanes (50 mL, 1:9), and dried in vacuo to give a light yellow solid (8.30 g, 72%) of sufficient purity for use in the subsequent reaction.

NMR (DMSO-d$_6$): δ8.91 (s, 1H), 8.05 (d,J=8.2 Hz, 1H), 7.84 (d,J=7.5 Hz, 1H), 7.67 (d,J=8.4 Hz, 1H), 7.51 (dd,J$_1$=7.0 Hz, J$_2$=8.2 Hz, 1H), 7.45 (dd,J$_1$=7.0 Hz, J$_2$=7.5 Hz, 1H), 7.42 (d,J=8.4 Hz, 1H), 5.37 (br s, 2H), 3.52 (s, 2H), 2.60 (s, 3H)

IR (KBr): 3500, 3380, 3060, 2780, 1675, 1595 cm$^{-1}$
MS (+CI): 215(M+H, 100)
Anal. Calcd for C$_{13}$H$_{14}$N$_2$O: C, 72.87; H, 6.59; N, 13.07%;
Found: C, 72.36; H, 6.41; N, 12.76%.

Step (8)

Preparation of 4-[(1-Methyl-2-naphthalenyl)methyl]-3H-1,2,3,5-oxathiadiazole 2-Oxide A suspension of N'-hydroxy-2-(1-methylnaphthalenyl)ethanimidamide (2.8 g, 13.1 mmol) in toluene (250 mL) was heated to 80° C. until all of the solid had dissolved. Thionyl chloride (1.86 g, 15.7 mmol) was added dropwise to the above solution under a stream of nitrogen, and a white precipitate was formed. The mixture was heated to reflux for 15 minutes, during which the precipitate dissolved to give an orange solution. The hot solution was filtered to remove trace solids and the filtrate was concentrated in vacuo to give a yellow solid. Recrystallization from toluene gave the desired product (1.90 g, 56%) as a light yellow solid, m.p. 118°-119° C. (dec.).

NMR (DMSO-d$_6$): δ11.43 (br s, 1H), 8.10 (d,J=8.4 Hz, 1H), 7.88 (d,J=8.5 Hz, 1H), 7.75 (d,J=8.4 Hz, 1H), 7.56 (t,J=8.5 Hz, 1H), 7.50 (t,J=8.5 Hz, 1H), 7.41 (d, J=8.5 Hz, 1H), 4.16 (s, 2H), 2.61 (s, 3H)

IR (KBr): 3420, 3150, 1390, 1180, 815 cm$^{-1}$,
MS (EI): 260(M+), 195(29), 154(100), 141(33),
Anal. Calcd for C$_{13}$H$_{12}$N$_2$O$_2$S: C, 59.98; H, 4.65; N, 10.76%;
Found: C, 60.21; H, 4.66; N, 10.63%.

EXAMPLE 4

4-[(5-Chloro-2-naphthalenyl)methyl]-3H-1,2,3,5-oxathiadiazole 2-Oxide

Step (1)

Preparation of Methyl 5-Bromo-2-naphthoate

To a boiling solution of 2-naphthoic acid (200 g, 1.16 mol) in acetic acid (1000 mL) was added dropwise bromine (60 mL, 2.2 mol) containing 5.0 g of iodine. After the addition was complete, the solution was refluxed for an additional 0.5 hour. After cooling the precipitated product was isolated by filtration, washed with acetic acid and water. The crude acid was treated with hot 1N sodium hydroxide solution (1000 mL). The resulting suspension was filtered to give the sodium salt of the carboxylic acid (107 g). On cooling the filtrate furnished an additional material (43 g, total 150 g). This was suspended in methanol (1L) and concentrated sulfuric acid (68 mL) was added gradually. This suspension was refluxed for 18 hours. After cooling, the resulting solution was evaporated to dryness in vacuo and the residue partitioned between methylene chloride and water. The aqueous layer was extracted with methylene chloride and the combined organic layers were washed with saturated sodium bicarbonate solution and with water. This was dried (MgSO$_4$) and evaporated in vacuo to give the crude title compound (116.5 g, 38%) as an oil which crystallized slowly on standing to an off-white solid, m.p. 65°-68° C. This compound was pure enough to be used as such in the next step.

Step (2)

Preparation of Methyl 5-Chloro-2-naphthoate

According to R. G. R. Bacon, et al., *J. Chem. Soc.* 1097 (1964) and H. Goldstein, et al., *Helv. Chim. Acta.* 21, 62 (1938), a mixture of methyl 5-bromo-2-naphthoate (35.0 g, 0.132 mol), copper (1) chloride (43.1 g, 0.436 mol) and dry DMSO (400 mL) was heated at 105°-110° C. for 6 hours under N$_2$. The mixture was cooled to room temperature, diluted with H$_2$O (250 mL) and ether (250 mL), and filtered through Celite. The layers were separated, and the organic phase was washed with H$_2$O/brine (1:1), 1NHCl, saturated aqueous NaHCO$_3$, dried (MgSO$_4$), and concentrated to give an off-white solid (28.7 g, 99%). The compound was used without further purification.

NMR (DMSO-d$_6$, 300 MHz): δ3.93 (s, 3H), 7.60 (m, 1H), 7.84 (dd,J=7.5 Hz, 0.9 Hz, 1H), 8.10 (dd,J=8.7 Hz, 1.8 Hz, 1H), 8.15 (d,J=8.4 Hz, 1H), 8.24 (d,J=9.0 Hz, 1H), 8.69 (d,J=1.8 Hz, 1H).

Step (3)

Preparation of 5-Chloro-2-hydroxymethylnaphthalene

To a cooled (0° C.) stirred solution of methyl 5-chloro-2-naphthoate (26.7 g, 0.121 mol) in THF (100 mL) was added 1M DIBAL in THF (266 mL, 0.266 mol) over 1 hour 30 minutes. The cooling bath was removed and stirring was continued for 1 hour. The mixture was recooled to 0° C. and 1N NaOH (275 mL) was added (slowly at first). Ether (200 mL) and H$_2$O (100 mL) were added and the mixture was stirred at room temperature for 1 hour. The layers were separated and the aqueous phase was extracted with ether. The combined extracts were dried (MgSO$_4$) and concentrated to give a white solid (23.2 g, 99%). 200 mg was recrystallized from toluene/hexane for analysis, m.p. 85°-87° C.

NMR (DMSO-d$_6$, 400 MHz): δ4.70 (d,J=5.7 Hz, 2H), 5.42 (t,J=5.7 Hz, 1H), 7.48 (m, 1H), 7.63 (m, 2H), 7.91 (d,J=7.8 Hz, 1H), 7.92 (s, 1H), 8.12 (d,J=8.6 Hz, 1H)

IR (KBr, cm$^{-1}$): 3300 (OH),
MS: m/e 192 (M+), 175 (M+-OH),
Anal. Calcd for C$_{11}$H$_9$ClO: C, 68.58; H, 4.71%;
Found: C, 68.92; H, 4.84%.

Step (4)

Preparation of 5-Chloro-2-chloromethylnaphthalene

According to the procedure of T. G. Squires, et al., *J. Org. Chem.* 40, 134 (1975), to a stirred solution of 5-chloro-2-hydroxymethylnaphthalene (17.0 g, 0.0882 mol) in dioxane (100 mL) was added ZnCl$_2$ (360 mg, 2.65 mmol), then tionyl chloride (21.0 g, 0.176 mol) (slightly exothermic). After 40 minutes, the mixture was concentrated, taken up in ether, and washed with saturated aqueous NaHCO$_3$/brine (1:4). The organic phase was dried (MgSO$_4$) and concentrated to give a white solid (18.2 g, 98%). 200 mg was recrystallized from hexane for analysis, m.p. 86°-88° C.

NMR (CDCl$_3$, 400 MHz): δ4.76 (s, 2H), 7.40 (m, 1H), 7.57 (d,J=7.4 Hz, 1H), 7.61 (d,J=8.8 Hz, 1H), 7.75 (d,J=8.2 Hz, 1H), 7.84 (s, 1H), 8.27 (d,J=8.8 Hz, 1H)
IR (KBr, cm$^{-1}$): 2980 (CH)
MS: m/e 210 (M+), 175 (M+-Cl)

Anal. Calcd for $C_{11}H_8Cl_2$: C, 62.59; H, 3.82%; Found: C, 62.47; H, 3.91%.

Step (5)

Preparation of 5-Chloro-2-naphthalenylacetonitrile

A mixture of 5-chloro-2-chloromethylnaphthalene (24.5 g, 0.116 mol), sodium cyanide (6.8 g, 0.139 mol), $H_2O$ (25 mL), and acetonitrile (225 mL) was heated under reflux for 6 hours. The mixture was concentrated and suspended in $H_2O$. The solid was collected by filtration, dissolved in acetone, treated with $MgSO_4$, and concentrated to give an off-white solid (22.4 g, 96%). 200 mg was recrystallized from toluene/hexane for analysis, m.p. 110°–111° C. The remaining product was used without further purification.

NMR (DMSO-$d_6$, 400 MHz): $\delta$4.27 (s, 2H), 7.54 (m, 1H), 7.64 (dd,J=8.7 Hz, 1.9 Hz, 1H), 7.71 (dd,J=7.4 Hz, 0.8 Hz, 1H), 7.97 (d,J=8.2 Hz, 1H), 7.99 (s, 1H), 8.20 (d,J=8.7 Hz, 1H)

IR (KBr, cm$^{-1}$): 2240 (CN)

MS: m/ed 201 (M+), 166 (M+-Cl)

Anal. Calcd for $C_{12}H_8ClN$: C, 71.47; H, 4.00; N, 6.94%;
Found: C, 71.40; H, 3.99; N, 6.78%.

Step (6)

Preparation of N'-Hydroxy-2-(5-chloronaphthalenyl)ethanimidamide

To a stirred solution of 5-chloro-2-naphthalenylacetonitrile (5.00 g, 0.0248 mol) and hydroxylamine hydrocloride (3.45 g, 0.0496 mol) in DMSO (50 mL) was added sodium methoxide (25 wt% in MeOH; 11.3 mL, 0.0496 mol). The resulting mixture was heated at 80° C. for 1 hour 30 minutes. The MeOH was removed under reduced pressure and the mixture was diluted with $H_2O$ (150 mL). A white precipitate formed and was collected by filtration (5.04 g, 87%). 200 mg was recrystallized from toluene for analysis, m.p. 133° C.

NMR (DMSO-$d_6$, 400 MHz): $\delta$3.47 (s, 2H), 5.50 (br s, 2H), 7.47 (m, 1H), 7.62 (m, 2H), 7.86 (d,J=7.1 Hz, 1H), 7.87 (s, 1H), 8.09 (d,J=8.7 Hz, 1H), 8.95 (s, 1H)

IR (KBr, cm$^{-1}$): 3490 and 3380 (NH, OH), 1660 (C=N)

MS: m/e 234 (m+), 217 (M+-OH),

Anal. Calcd for $C_{12}H_{11}ClN_2O$: C, 61.48; H, 4.72; N, 11.94%;
Found: C, 61.44; H, 5.014; N, 11.71%.

Step (7)

Preparation of 4-[(5-Chloro-2-naphthalenyl)methyl]-3H-1,2,3,5-oxathiadiazole 2-Oxide To a cooled (0° C.) stirred suspension of N'-hydroxy-2-(5chloronaphthalenyl)ethanimidamide (4.8 g, 0.0205 mol) in dichloromethane (30 mL) was added pyridine (3.2 g, 0.0409 mol) all at once and a solution of thionyl chloride (2.7 g, 0.0225 mol) in dichloromethane (10 mL) over 5 minutes. After 25 minutes, $H_2O$ (150 mL) was added and the resulting yellow solid was collected by filtration (4.5 g). The crude product was recyrstallized from iPrOH (35 mL) to give an off-white solid (3.5 g, 61%) m.p. 169°–170° C.

NMR (DMSO-$d_6$, 400 MHz): $\delta$4.16 (s, 2H), 7.52 (m, 1H), 7.61 (dd,J=8.7 Hz, 1.7 Hz, 1H), 7.69 (dd,J=7.5 Hz, 1.0 Hz, 1H), 7.90 (d,J=8.3 Hz, 1H), 7.94 (s, 1H), 8.16 (d,J=8.7 Hz, 1H), 11.52 (s, 1H)

IR (KBr, cm$^{-1}$): 3400 (NH)

MS: m/e 280 (M+)

Anal. Calcd for $C_{12}H_9ClN_2O_2S$: C, 51.34; H, 3.23; N, 9.98%;
Found: C, 51.24; H, 3.35; N, 9.68%.

The required naphthalenealkanols were prepared by the procedure of Example 3, Step 3; Step 4; and alternate Step 4 herein above.

The required naphthalenealkanols may also be prepared by the procedure of Example 5 herein below.

EXAMPLE 5

Preparation of 3-Methyl-2-naphthalenemethanol

A solution of 3-methyl-2-naphthoic acid (5.0 g, 26.9 mmol) in anhydrous THF (75 mL) was cooled to 0° C. and treated with lithium aluminum hydride (1M in THF, 26.9 mL, 26.9 mmol) added dropwise. After the addition was complete, the resulting mixture was stirred 5 minutes at 0° C., the ice bath was removed, the mixture warmed to room temperature and stirred a total of 20 hours. The mixture was cooled to 0° C. and quenched by dropwise addition of water (1.02 mL), followed by 15% NaOH (1.02 mL), and more water (3 mL). The resulting mixture was stirred 1 hour and the granular precipitate removed by filtration through a plug of Florosil and anhydrous magnesium sulfate. The filtrate was concentrated in vacuo, to give the desired product (4.6 g, 99%) as a white crystalline solid of sufficient purity for use in the subsequent reaction.

The required naphthalenylalkylnitriles were prepared by the process of Example 3, Step 6 herein above.

The required naphthalenylalkylnitriles may also be prepared by the procedure of Example 6 herein below.

EXAMPLE 6

Preparation of 3-Methyl-2-naphthalenylacetonitrile

KCN (1.81 g, 27.85 mmol) was added to a solution of 2-bromomethyl-3-methylnaphthalene (5.95 g, 25.32 mmol) in 150 mL of DMSO at room temperature. The resulting mixture was stirred 1 hour, diluted with water (175 mL) and stirred another 15 minutes. The resulting precipitate was collected by filtration, washed with water and dried in vacuo to give the desired product (3.71 g g, 81%) of sufficient purity for use in the subsequent reaction.

The required amidoximes were prepared by the process of Example 3, Step 7 herein above.

The required amidoximes may also be prepared by procedure of Example 7 herein below.

EXAMPLE 7

Preparation of N'-Hydroxy-2-(1-bromonaphthalenyl)ethanimidamide

Hydroxylamine hydrochloride (2.83 g, 40.7 mmol) was added in one portion to a solsution of NaOEt, freshly prepared from sodium (0.94 g, 40.7 mmol) in ethanol (200 mL). The resulting mixture was stirred 1 hour at room temperature, during which a precipitate was formed. 1-Bromo-2-naphthalenylacetonitrile (6.7 g, 27.0 mmol) was added in one portion and the resulting mixture heated to reflux a total of 12 hours. The mixture was cooled to room temperature and concentrated in vacuo. The residue was dissolved in EtOAc, washed with water (3×100 mL), brine, dried over anhydrous sodium sulfate, and concentrated in vacuo to give the amidoxime (6.97 g, 93%) as a light yellow solid of sufficient purity for use in the subsequent reaction.

The requried amidoximes may also be prepared by procedure of Example 8 herein below.

EXAMPLE 8

Preparation of N'-Hydroxy-2-(7-bromonaphthalenyl)ethanimidamide

Hydroxylamine hydrochloride (1.14 g, 16.5 mmol) was dissolved in aqueous sodium hydroxide (1N, 16.5 mL, 16.5 mmol) and the solution diluted with DMSO (50 mL). 7-Bromo-2-naphthalenylacetonitrile (1.35 g, 5.5 mmol) was added in one portion and the resulting mixture heated to 60° C. After a total of 18 hours, the mixture was cooled to room temperature and diluted with water (100 mL) to give a precipitate. The precipitate was collected by filtration, washed with water, and dried in vacuo to give a tan solid (1.24 g, 81%) which was of sufficient purity for use in the subsequent reaction.

The naphthalenylalkyl-3H-1,2,3,5-oxathiadiazole 2-oxides listed in the Table below were prepared by the procedure described above in Example 3, Step 8, or said compounds may also be prepared by the procedure of Example 1, Step 7 herein above.

TABLE 1

TABLE OF MELTING POINTS OF FINAL PRODUCTS

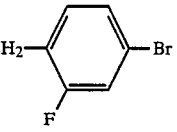

| $R^1$ | $R^2$ | n | m.p. °C. |
|---|---|---|---|
| 5-Br | —H | 1 | 159–160 |
| 8-Br | —H | 1 | 157–158 |
| 1-Br | —H | 1 | 141–143 |
| 3-CH$_3$ | —H | 1 | 146–147 (dec.) |
| 5-Br | —H | 2 | tacky solid |
| 5-Cl | —H | 1 | 164–165 |
| 1-CH$_3$ | —H | 1 | 118–119 (dec.) |
| 1-Cl | —H | 1 | 130–132 (dec.) |
| 3-OCH$_3$ | —H | 1 | 143–145 (dec.) |
| 3-Cl | —H | 1 | 161–162 (dec.) |
| 1-OCH$_3$ | 4-Cl | 1 | 148–149 (dec.) |
| 1-OCH$_3$ | —H | 1 | 14.25–144 (dec.) |
| 1-Br | 3-CH$_3$ | 1 | 175–176 |
| 1-F | —H | 1 | 158–159 |
| 5-CF$_3$ | —H | 1 | 175–176 |
| 5-CH$_3$ | —H | 1 | 155.5–157 |
| 3-CF$_3$ | —H | 1 | 145–146 |
| 5-C≡CH | —H | 1 | 175–176 |
| 8-Cl | —H | 1 | 149–150 |
| —H | —H | 2 | 114–115 |
| 6-Br | —H | 1 | 164–165 |
| 3-Br | —H | 1 | 153–154 |
| 4-Br | —H | 1 | 164–165 |
| 7-CH$_3$ | 8-Br | 1 | 175.5–176 |
| 1-Br | 6-F | 1 | 150–151 |
| 5-OCH$_3$ | 8-Br | 1 | 164–165 (dec.) |
| 7-OCH$_3$ | —H | 1 | 147–148 |
| 3-CH$_3$ | —H | 2 | — |
| 5-C$_2$H$_5$ | —H | 1 | 145–147 |
| 1-C$_2$H$_5$ | —H | 1 | 106–107 |
| 5-Br | 8-SCH$_3$ | 1 | 173 |
| —H | — | 1 | 148–151 (dec.) |
| 7-CH$_3$ | —H | 1 | 165–166 |

TABLE 1-continued

TABLE OF MELTING POINTS OF FINAL PRODUCTS

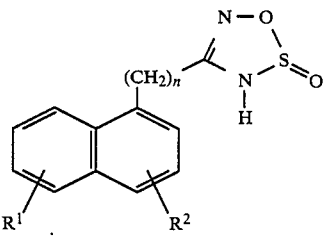

| | —H | 1 | 176–178 (dec.) |
|---|---|---|---|
| 1-Cl | 6-F | 1 | 153–154 |
| 7-Cl | —H | 1 | 185 |
| 5-OCH$_3$ | —H | 1 | 139–140.5 |
| 8-CN | —H | 1 | 177–178.5 |
| 6-F | —H | 1 | 168–169 |
| —H | —H | 3 | 139–140 |
| 6-OCH$_3$ | —H | 1 | 146–147 |
| —H | —H | 0 | 137–138 (dec.) |
| 6-OCH$_3$ | —H | 0 | 145–146 (dec.) |
| —H | —H | 4 | 94–95 |
| 1-NO$_2$ | —H | 1 | 155–156 (dec.) |
| 1-NO$_2$ | 4-OCH$_3$ | 1 | 171–174 (dec.) |
| 1-OCH$_3$ | 4-Br | 1 | 140–141 |
| 5-SCH$_3$ | —H | 1 | 151–152 |
| 1-CH$_3$ | 3-CH$_3$ | 1 | 152–154 (dec.) |
| 7-Br | —H | 1 | — |

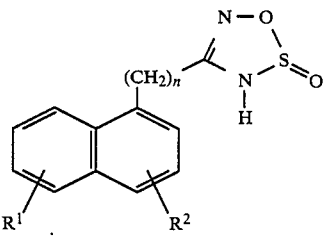

| $R^1$ | $R^2$ | n | m.p. °C. |
|---|---|---|---|
| —H | —H | 1 | 138–140 (dec.) |
| 8-CH$_3$ | —H | 1 | 137–139 (dec.) |
| 2-CH$_3$ | —H | 1 | >110 (slow dec.) |
| 3-Br | 4-OCH$_3$ | 1 | >122 (slow dec.) |
| 4-Br | —H | 1 | 160–162 (dec.) |
| 4-CH$_3$ | —H | 1 | >130 (slow dec.) |
| 5-CF$_3$ | 6-OCH$_3$ | 1 | 139–141 |
| 8-Br | —H | 1 | 155–157 (dec.) |
| 5-Br | —H | 1 | >110 (slow dec.) |
| 2-OCH$_3$ | —H | 1 | >125 (slow dec.) |
| 2-OCH$_3$ | 6-Br | 1 | >120 (slow dec.) |
| 2-NO$_2$ | —H | 1 | 162–164 (dec.) |

The blood glucose lowering activity of the compounds of this invention was demonstrable in experiments using diabetic (db/db) mice. The db/db (C57BL/KsJ) mouse exhibits many metabolic abnormalities that are associated with non-insulin dependent diabetes mellitus (Type II) in humans. The animals are obese, glucose intolerant and have fasting hyperglycemia which is sometimes accompanied by a paradoxical hyperinsulinemia. Furthermore, the db/db mouse will eventually develop some of the long-term complications that have been associated with diabetes mellitus. [See Coleman *Diabetes* 31 (Suppl. 1), 1 (1982)]. In spite of these commonalities, the acute administration of sulfonylureas (even at extremely high dosages) will not reduce the hyperglycemia of the db/db mouse. [See Tutwiler et al, *Diabetes* 27, 856 (1978)]. The ability of a few other hypoglycemic agents to be effective in this species suggest that the other agents have mechanisms of action which are different from that of the sulfonylureas [ibid; Lee et al, *Diabetes* 31:12 (1982); Chang et al, *Diabetes* 32, 830 (1983); Hosokawa et al, *Diabetes* 34, 267 (1985)]. Such compounds, therefore, are more likely to be efficacious in the population of Type II diabetic patients that do not respond to sulfonylurea therapy. The experimental results are exemplified hereinbelow after the listing of the following general procedure pertaining to these experiments.

POSTPRANDIAL ASSAY PROCEDURE

On the morning of Day 1, 35 mice [mal db/db (C57BL/KsJ), Jackson Laboratories, 2 to 7 months of age and body weight 35 to 60 g] were fasted for 4 hours, weighed and a baseline blood sample was collected from the tail-tip of each mouse without anesthesia, placed directly into a fluoride-containing tube, mixed and maintained on ice. Food was then returned to the mice. The plasma was separated and levels of glucose in plasma determined by the Abbott VP Analyser. Because of the variable plasma glucose levels of the db/db mice, 5 mice having the most extreme (i.e., highest or lowest) plasma glucose levels were excluded and the remaining 30 mice were randomly assigned into 7 groups of equivalent mean plasma glucose levels:

| Group A: | Vehicle control | N = 6 |
|---|---|---|
| Group B: | Positive control (ciglitazone) | N = 4 |
| Group C: | 1st Test drug | N = 4 |
| Group D: | 2nd Test drug | N = 4 |
| Group E: | 3rd Test drug | N = 4 |
| Group F: | 4th Test drug | N = 4 |
| Group H: | 5th Test drug | N = 4 |

On the afternoon of Days 1, 2 and 3 the vehicle, control or test drugs were administered (p.o.) to the ad libitum fed mice. The positive control, ciglitazone [(+)-5-[4-[(1-methylcyclohexy]methoxyl]benzyl]-thiazolidine-2,4-dione] see Fujita et al., *Diabetes* 32 804 (1983), was given by gavage at a dose of 100 mg/kg/day. The test compounds were given by gavage at a dose of 100 mg/kg/day unless otherwise noted in Table 2.

On the morning of Day 4, the mice were weighed and food removed, but water was available ad libitum. Three hours later, a blood sample was collected and then the mice were given the fourth administration of drug or vehicle. Blood samples were collected again from the unanesthetized mice at 2 and 4 hours after drug administration. The plasma was separated and levels of glucose in plasma determined by the Abbott VP Analyser.

For each mouse, the percent change of its plasma glucose level on Day 4 (mean of the 2 and 4 hour samples) from its respective level before drug administration (Day 1 baseline sample) was determined as follows:

$$\frac{\text{Mean of 2 and 4 hour Samples (Day 4)}}{\text{Baseline Sample (Day 1)}} \times 100$$

Analysis of variance followed by Dunnett's multiple comparison (one-sided) was used to estimate the degree of statistical significance of the difference between the vehicle control group and the individual drug-treated groups.

INSULIN TOLERANCE TEST ASSAY PROCEDURE

Alternatively, some compounds were evaluated for their ability to lower the plasma glucose of diabetic db/db mice during an insulin tolerance test (ITT).

On the morning of Day 1, 25 mice [male db/db (C57BL/KsJ), Jackson Laboratories, 2 to 7 months of age and body weight 35 to 60 g] were fasted for 4 hours, weighed and a baseline blood sample was collected from the tail-tip of each mouse without anesthesia, placed directly into a fluoride-containing tube, mixed and maintained on ice. Food was then returned to the mice. The plasma was separated and levels of glucose in plasma determined by the Abbott VP Analyzer. Because of the variable plasma gluocose levels of the db/db mice, 5 mice having the most extreme (i.e., highest or lowest) plasma glucose levels were excluded and the remaining 20 mice were randomly assigned into 5 groups of equivalent mean plasma glucose levels:

Group A: Vehicle Control
Group B: Positive Control (ciglitazone)
Group C: 1st Test Drug
Group D: 2nd Test Drug
Group E: 3rd Test Drug On the afternoon of Days 1, 2, and 3, the vehicle, control or test drug were administered (p.o.) to the ad liubitum fed mice. The mice were then fasted 18-24 hours and the fourth dose was administered on the morning of Day 4, immediately after the collection of the baseline blood sample. Additional blood samples were collected at 90 and 120 minutes after drug administration. Insulin was immediately administered (0.5 U/kg, s.c.) to every mouse after the 120 minutes sample. Serial blood samples were collected similarly at 45 and 120 minutes, after insulin administration (165 and 240 minutes, respectively, after the drug administration). The plasma was separated and levels of glucose in plasma determined by the Abbott VP Analyzer.

Analysis of variance followed by Dunnett's Multiple Comparison (one-sided) was used to estimate the degree of statistical significance of the difference between the plasma glucose level of the vehicle control and the individual drug-treated groups at each time. Statistical significance of the difference between the percent charge of the vehicle control and the individual drug-treated groups at each time was determined by analysis of variance followed by Dunnett's Multiple Comparison (one-sided).

The tabulated results in Table 2 show that the oxathiadiazoles of this invention show the property that they lower blood glucose levels in the diabetic (db/db) mice using the postprandial assay procedure. The actual difference between the mean percent change of the vehicle and the drug-treated group is reported in Table 2.

TABLE 2
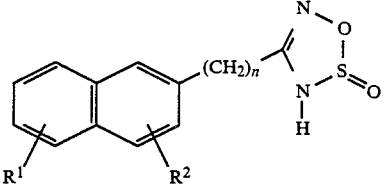
| $R^1$ | $R^2$ | n | Dose mg/kg/day | % Change from Vehicle in Postprandial Plasma Glucose |
|---|---|---|---|---|
| 8-Br | —H | 1 | 5 | −59 |
|  |  |  | 1 | −48 |
| 5-Br | —H | 1 | 20 | −59 |
|  |  |  | 5 | −47 |
|  |  |  | 1 | −35 |
| 3-CH$_3$ | —H | 1 | 5 | −36 |
|  |  |  | 1 | −26 |
| 5-Br | —H | 2 | 5 | −33 |
|  |  |  | 1 | −26 |
| 5-Cl | —H | 1 | 5 | −51 |
|  |  |  | 1 | −21 |
| 1-CH$_3$ | —H | 1 | 5 | −36 |
|  |  |  | 1 | −20 |
| 5-C≡CH | —H | 1 | 5 | −45 |
|  |  |  | 1 | −19 |
| 1-OCH$_3$ | 4-Br | 1 | 5 | −26 |
|  |  |  | 1 | −18 |
| 1-OCH$_3$ | 4-Cl | 1 | 5 | −31 |
|  |  |  | 1 | −17 |
| 3-OCH$_3$ | —H | 1 | 20 | −50 |
|  |  |  | 1 | −16 |
| 8-Cl | —H | 1 | 5 | −55 |
|  |  |  | 1 | −14 |
| 1 | CH$_3$ | 1 | 5 | −45 |
|  |  |  | 1 | −11 |
| 3-Cl | —H | 1 | 5 | −44 |
|  |  |  | 1 | −14 |
| 1-Br | —H | 1 | 20 | −63 |
|  |  |  | 5 | −33 |
|  |  |  | 1 | −11 |
| 1-OCH$_3$ | —H | 1 | 5 | −43 |
|  |  |  | 1 | −8 |
| 1-F | —H | 1 | 5 | −39 |
|  |  |  | 1 | −2 |
| 5-CH$_3$ | —H | 1 | 5 | −37 |
|  |  |  | 1 | +7 |
| 1-Br | 3-CH$_3$ | 1 | 5 | −34 |
|  |  |  | 1 | −12 |
| 3-CF$_3$ | —H | 1 | 5 | −30 |
|  |  |  | 1 | −8 |
| 5-CF$_3$ | —H | 1 | 5 | −30 |
|  |  |  | 1 | −9 |
| 3-Br | —H | 1 | 5 | −28 |
|  |  |  | 1 | −12 |
| 1-Cl | —H | 1 | 20 | −64 |
|  |  |  | 5 | −27 |
|  |  |  | 1 | −13 |
| 6-Br | —H | 1 | 5 | −25 |
|  |  |  | 1 | 0 |
| 1-C$_2$H$_5$ | —H | 1 | 5 | −24 |
|  |  |  | 1 | −6 |
| 5-C$_2$H$_5$ | —H | 1 | 5 | −23 |
|  |  |  | 1 | −2 |
| 7-CH$_3$ | 8-Br | 1 | 5 | −21 |
| 4-Br | —H | 1 | 5 | −21 |
|  |  |  | 1 | — |
| 7-OCH$_3$ | —H | 1 | 5 | −19 |
| 5-Br | 8-SCH$_3$ | 1 | 5 | −19 |
|  |  |  | 1 | +13 |
| —H | —H | 1 | 100 | −63 |
|  |  |  | 20 | −37 |
|  |  |  | 5 | −18 |
| 5-CH=CH$_2$ | —H | 1 | 5 | −17 |
| 1-Br | 6-F | 1 | 5 | −16 |

TABLE 2-continued
| R1 | R2 | n | Dose | % Change |
|---|---|---|---|---|
| 5-OCH3 | —H | 1 | 5 | −15 |
|  |  |  | 1 | +3 |
| 1-Cl | 6-F | 1 | 5 | −14 |
| 8-CN | —H | 1 | 5 | −10 |
|  |  |  | 1 | −3 |
| 7-Br | — | 1 | 5 | −7 |
| 7-Cl | —H | 1 | 5 | −5 |
| 3-OCH2—C6H3(Br)(F) | —H | 1 | 5 | −1 |
| —H | —H | 2 | 20 | −38 |
| 7-CH3 | —H | 1 | 20 | −36 |
| 6-F | —H | 1 | 100 | −62 |
|  |  |  | 20 | −26 |
| —H | —H | 3 | 100 | −25 |
|  |  |  | 20 | −9 |
| 6-OCH3 | —H | 0 | 20 | −5 |
| 6-OCH3 | —H | 1 | 100 | −27 |
|  |  |  | 20 | +4 |
| —H | —H | 0 | 20 | +6 |
| —H | —H | 4 | 100 | −28 |
| 3-CH3 | —H | 2 | 1 | +9 |
| 5-OCH3 | 8-Br | 1 | 1 | −13 |
| 5-SCH3 | —H | 1 | 5 | −4 |
| 1-NO2 | —H | 1 | 20 | −49 |
| 1-NO2 | 4-OCH3 | 1 | 5 | −4 |
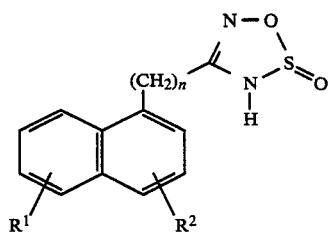
| R1 | R2 | n | Dose mg/kg/day | % Change from Vehicle in Postprandial Plasma Glucose |
|---|---|---|---|---|
| 8-CH3 | —H | 1 | 20 | −33 |
| 2-CH3 | —H | 1 | 20 | −32 |
| —H | —H | 1 | 20 | −4 |
| 3-Br | 4-OCH3 | 1 | 20 | −54 |
|  |  |  | 1 | −15 |
| 4-Br | —H | 1 | 20 | −23 |
|  |  |  | 5 | −14 |
| 4-CH3 | —H | 1 | 20 | −17 |
| 5-CF3 | 6-OCH3 | 1 | 20 | −10 |
| 8-Br | —H | 1 | 20 | −30 |
|  |  |  | 5 | −24 |
| 5-Br | —H | 1 | 20 | −15 |
| 2-OCH3 | 6-Br | 1 | 20 | −10 |
| 2-OCH3 | —H | 1 | 20 | −22 |
| 2-NO2 | —H | 1 | 5 | −1 |
| Ciglitazone (reference standard) |  |  | 100 | −33 |
We claim:
1. A compound of formula (I)
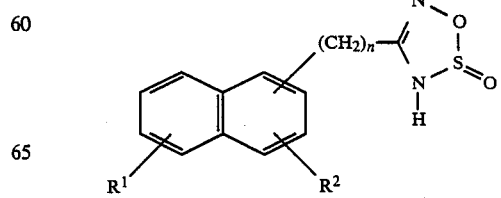

wherein $R^1$ and $R'$ are independently hydrogen, lower alkyl containing 1 to 6 carbon atoms, alkoxy containing 1 to 6 carbon atoms, halogen, ethynyl, nitrile, methylthio, trifluoromethyl, vinyl, nitro or halogen substituted benzyloxy; or n is 0 to 4 or the pharmaceutically acceptable salts thereof.

2. A compound according to claim 1 of formula (II)

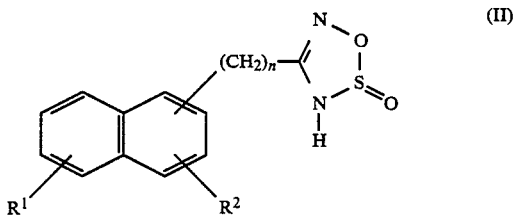

(II)

wherein $R^1$ and $R^2$ are independently hydrogen, lower alkyl containing 1 to 6 carbon atoms, alkoxy containing 1 to 6 carbon atoms, halogen, ethynyl, nitrile, trifluoromethyl, vinyl or nitro; n is 1 or 2 or the pharmaceutically acceptable salts thereof.

3. The compound according to claim 2 4-[(5-bromo-2-naphthalenyl)methyl]-3H-1,2,3,5-oxathiadiazole 2-oxide or the pharmaceutically acceptable salts thereof.

4. The compound according to claim 2 4-[(8-bromo-2-naphthalenyl)methyl]-3H-1,2,3,5-oxathiadiazole 2-oxide or the pharmaceutically acceptable salts thereof.

5. The compound according to claim 2 4-[(1-bromo-2-naphthalenyl)melthyl]-3-H-1,2,3,5-oxathiadiazole 2-oxide or the pharmaceutically acceptable salts thereof.

6. The compound according to claim 2 4-[(3-methyl-2-napthalenyl)methyl]-3H-1,2,3,5-oxathiadiazole 2-oxide or the pharmaceutically acceptable salts thereof.

7. The compound according to claim 2 4-[2-(5-bromo-2-naphthalenyl)ethyl]-3H-1,2,3,5-oxathiadiazole 2-oxide or the pharmaceutically acceptable salts thereof.

8. The compound according to claim 2 4-[(5-chloro-2-naphthalenyl)methyl]-3H-1,2,3,5-oxathiadiazole 2-oxide or the pharmaceutically acceptable salts thereof.

9. The compound according to claim 2 4-[(1-methyl-2-naphthalenyl)methyl]-3H-1,2,3,5-oxathiadiazole 2-oxide or the pharmaceutically acceptable salts thereof.

10. The compound according to claim 2 4-[(1-chloro-2-naphthalenyl)methyl]-3H-1,2,3,5-oxathiadiazole 2-oxide or the pharmaceutically acceptable salts thereof.

11. The compound according to claim 2 4-[(3-methoxy-2-naphthalenyl)methyl-3H-1,2,3,5-oxathiadiazole 2-oxide or the pharmaceutically acceptable salts thereof.

12. The compound according to claim 2 4-[(3-chloro-2-naphthalenyl)methyl]-3H-1,2,3,5-oxathiadiazole 2-oxide or the pharmaceutically acceptable salts thereof.

13. The compound according to claim 2 4-[(4-chloro-1-methoxy-2-naphthalenyl)methyl]-3H-1,2,3,5-oxathiadiazole 2-oxide or the pharmaceutically acceptable salts thereof.

14. The compound according to claim 2 4-[(1-methoxy-2-naphthalenyl)melthyl]-3H-1,2,3,5-oxathiadiazole 2-oxide or the pharmaceutically acceptable salts thereof.

15. The compound according to claim 2 4-[(1-bromo-3-methyl-2-naphthalenyl)methyl]-3H-1,2,3,5-oxathiadiazol 2-oxide or the pharmaceutically acceptable salts thereof.

16. The compound according to claim 2 4-[(1-fluoro-2-naphthalenyl)methyl]-3H-1,2,3,5-oxathiadiazole 2-oxide or the pharmaceutically acceptable salts thereof.

17. The compound according to claim 2 4-[[5-(trifluoromelthyl)-2-naphthalenyl]methyl]-3H-1,2,3,5-oxathiadiazole 2-oxide or the pharmaceutically acceptable salts thereof.

18. The compound according to claim 2 4-[(5-methyl-2-naphthalenyl)methyl]-3H-1,2,3,5-oxathiadiazole 2-oxide or the pharmaceutically acceptable salts thereof.

19. The compound according to claim 2 4-[[3-(trifluoromethyl)-2-naphthalenyl]methyl]-3H-1-,2,3,5-oxathiadiazole 2-oxide or the pharmaceutically acceptable salts thereof.

20. The compound according to claim 2 4-[(5-ethynyl-2-naphthalenyl)methyl]-3H-1,2,3,5-oxathiadiazole 2-oxide or the pharmaceutically acceptable salts thereof.

21. The compound according to claim 2 4-[(8-chloro-2-naphthalenyl)methyl]-3H-1,2,3,5-oxathiadiazole 2-oxide or the pharmaceutically acceptable salts thereof.

22. The compound according to claim 2 4-[(4-bromo-1-methoxy-2-naphthalenyl)methyl]-3H-1,2,3,5-oxathiadiazole 2-oxide or the pharmaceutically acceptable salts thereof.

23. The compound according to claim 2 4-[(1-nitro-2-naphthalenyl)methyl]-3H-1,2,3,5-oxathiadiazole 2-oxide or the pharmaceutically acceptable salts thereof.

24. The compound according to claim 2 4-[(8-bromo-1-naphthalenyl)methyl]-3H-1,2,3,5-oxathiadiazole 2-oxide or the pharmaceutically acceptable salts thereof.

25. The compound according to claim 2 4-[(3-bromo-4-methoxy-1-naphthalenyl)methyl]-3H-1,2,3,5-oxathiadiazole 2-oxide or the pharmaceutically acceptable salts thereof.

26. A method of treating non-insulin dependent diabetes mellitus in humans by administering an effective amount of the compound of claim 1.

27. A pharmaceutical composition useful for treating non-insulin dependent diabetes mellitus in humans comprising an effective amount of a compound of claim 1 and a pharmaceutically acceptable carrier.

* * * * *